US011649291B2

(12) United States Patent
Griswold et al.

(10) Patent No.: US 11,649,291 B2
(45) Date of Patent: May 16, 2023

(54) ANTIBODIES AND METHODS OF MAKING SAME

(71) Applicant: Insmed Incorporated, Bridgewater, NJ (US)

(72) Inventors: Karl Edwin Griswold, Lyme, NH (US); Chris Bailey-Kellogg, Strafford, VT (US); Yoonjoo Choi, Gyeonggi-do (KR)

(73) Assignee: Insmed Incorporated, Bridgewater, NJ (US)

( * ) Notice: Subject to any disclaimer, the term of this patent is extended or adjusted under 35 U.S.C. 154(b) by 249 days.

(21) Appl. No.: 16/303,530

(22) PCT Filed: May 24, 2017

(86) PCT No.: PCT/US2017/034175
§ 371 (c)(1),
(2) Date: Nov. 20, 2018

(87) PCT Pub. No.: WO2017/205465
PCT Pub. Date: Nov. 30, 2017

(65) Prior Publication Data

US 2020/0317792 A1 Oct. 8, 2020

Related U.S. Application Data

(60) Provisional application No. 62/340,985, filed on May 24, 2016.

(51) Int. Cl.
*C07K 16/28* (2006.01)
*A61K 45/06* (2006.01)

(52) U.S. Cl.
CPC .......... *C07K 16/2863* (2013.01); *A61K 45/06* (2013.01); *C07K 2317/24* (2013.01); *C07K 2317/565* (2013.01)

(58) Field of Classification Search
CPC ............ C07K 16/2863; C07K 2317/24; C07K 2317/565; A61K 45/06
See application file for complete search history.

(56) References Cited

U.S. PATENT DOCUMENTS

| | | | |
|---|---|---|---|
| 4,444,887 | A | 4/1984 | Hoffmann |
| 4,716,111 | A | 12/1987 | Osband et al. |
| 5,223,409 | A | 6/1993 | Ladner et al. |
| 5,403,484 | A | 4/1995 | Ladner et al. |
| 5,427,908 | A | 6/1995 | Dower et al. |
| 5,516,637 | A | 5/1996 | Huang et al. |
| 5,530,101 | A | 6/1996 | Queen et al. |
| 5,545,806 | A | 8/1996 | Lonberg et al. |
| 5,565,332 | A | 10/1996 | Hendricus et al. |
| 5,571,698 | A | 11/1996 | Ladner et al. |
| 5,580,717 | A | 12/1996 | Dower et al. |
| 5,585,089 | A | 12/1996 | Queen et al. |
| 5,639,641 | A | 6/1997 | Pedersen et al. |
| 5,658,727 | A | 8/1997 | Barbars et al. |
| 5,698,426 | A | 12/1997 | Huse |
| 5,733,743 | A | 3/1998 | Johnson et al. |
| 5,750,753 | A | 5/1998 | Kimae et al. |
| 5,780,225 | A | 7/1998 | Wigler et al. |
| 5,814,318 | A | 9/1998 | Lonberg et al. |
| 5,821,047 | A | 10/1998 | Garrard et al. |
| 5,969,108 | A | 10/1999 | McCafferty et al. |
| 7,132,510 | B2 | 11/2006 | Hagay et al. |
| 9,051,370 | B2 | 6/2015 | Goletz et al. |
| 10,647,756 | B2 * | 5/2020 | Finlay .................. C07K 16/464 |
| 2010/0190247 | A1 | 7/2010 | Lazar et al. |
| 2011/0301331 | A1 | 12/2011 | Glaser et al. |
| 2013/0273033 | A1 | 10/2013 | Goletz et al. |
| 2015/0071923 | A1 | 3/2015 | Wei et al. |
| 2016/0068609 | A1 | 3/2016 | Goletz et al. |

FOREIGN PATENT DOCUMENTS

| | | | |
|---|---|---|---|
| CN | 103025760 | A | 4/2013 |
| EP | 0 239 400 | A2 | 9/1987 |
| EP | 0 519 596 | A1 | 12/1992 |
| EP | 0 592 106 | A1 | 4/1994 |
| WO | WO 90/02809 | A1 | 3/1990 |
| WO | WO 91/09967 | A1 | 7/1991 |
| WO | WO 91/10737 | A1 | 7/1991 |
| WO | WO 91/10741 | A1 | 7/1991 |
| WO | WO1992/001047 | A1 | 1/1992 |
| WO | WO 92/18619 | A1 | 10/1992 |

(Continued)

OTHER PUBLICATIONS

Abhinandan et al. (2008) "Analysis and improvements to Kabat and structurally correct numbering of antibody variable domains", Molecular Immunology, 45, pp. 3832-3839.
Aggarwal S.R. (2014) "What's fueling the biotech engine—2012 to 2013". Nature Biotechnology, vol. 32, No. 1, pp. 32-39.
Baca et al. (1997) "Antibody humanization using monovalent phage display", Journal of Biological Chemistry, vol. 272, No. 16, pp. 10678-10684.
Chen et al. (2009) "Computational structure-based redesign of enzyme activity", Proceedings of the National Academy of Sciences, vol. 106, No. 10, pp. 3764-3769.
Choi et al. (2015) "Antibody humanization by structure-based computational protein design", mAbs, 7:6, pp. 1045-1057.
Chothia et al. (1998) "Structural determinants in the sequences of immunoglobulin variable domain", Journal of Molecular Biology, 278, pp. 457-479.

(Continued)

*Primary Examiner* — Julie Wu
*Assistant Examiner* — Cheom-Gil Cheong
(74) *Attorney, Agent, or Firm* — Winstead PC

(57) ABSTRACT

Provided are variants of a chimeric anti-EGFR antibody. In various embodiments, the variants exhibit substantially improved thermostabilities and/or substantially higher levels of humanness, while retaining binding affinity near the parental level. The consistently high quality of the turnkey CoDAH designs, over a whole panel of variants, suggests that a computationally-directed approach encapsulates key determinants of antibody structure and function.

6 Claims, 15 Drawing Sheets

Specification includes a Sequence Listing.

(56) References Cited

FOREIGN PATENT DOCUMENTS

| | | | |
|---|---|---|---|
| WO | WO 93/11236 | A1 | 6/1993 |
| WO | WO 95/15982 | A2 | 6/1995 |
| WO | WO 95/20401 | A1 | 8/1995 |
| WO | WO 96/33735 | A1 | 10/1996 |
| WO | WO 96/34096 | A1 | 10/1996 |
| WO | WO 96/40210 | A1 | 12/1996 |
| WO | WO 98/16654 | A1 | 4/1998 |
| WO | WO 98/24893 | A2 | 6/1998 |
| WO | WO 98/46645 | A2 | 10/1998 |
| WO | WO 98/50433 | A2 | 11/1998 |
| WO | WO 99/60023 | A1 | 11/1999 |
| WO | WO 00/69459 | A1 | 11/2000 |
| WO | WO 02/45653 | A2 | 6/2002 |
| WO | WO 2004/085474 | A2 | 10/2004 |
| WO | WO 2005/051355 | A1 | 6/2005 |
| WO | WO 2007/127936 | A2 | 11/2007 |
| WO | WO 2009/062083 | A2 | 5/2009 |
| WO | WO 2010/056893 | A1 | 5/2010 |
| WO | WO 2010/080463 | A1 | 7/2010 |
| WO | WO 2012/020059 | A1 | 2/2012 |
| WO | WO 2013092998 | A1 | 6/2013 |
| WO | WO 2014173886 | A1 | 10/2014 |

OTHER PUBLICATIONS

Chothia et al. (1985) "Domain association in immunoglobulin molecules: the packing of variable domains", Journal of Molecular Biology, 186, pp. 651-663.
Clark M. (2000) "Antibody humanization: a case of the 'Emperor's new clothes'?", Immunology Today, vol. 21, No. 8 pp. 397-402.
Dall'acqua et al. (2005) "Antibody humanization by framework shuffling", Methods, 36, pp. 43-60.
Dennis M.S. (2010), Current Trends in Monoclonal Antibody Development and Manufacturing, Springer, Chapter 2 pp. 9-28.
Duvall et al., "A novel platform to produce human monoclonal antibodies: The next generation of therapeutic human monoclonal antibodies discovery", MAbs, 3:2, pp. 203-208.
Feldhaus et al. (2003) "Flow-cytometric isolation of human antibodies from a nonimmune *Saccharomyces cerevisiae* surface display library", Nature Biotechnology, vol. 21, pp. 163-170.
Foote et al. (1992) "Antibody framework residues affecting the conformation of the hypervariable loops", Journal of Molecular Biology, 224, pp. 487-499.
Frokjaer et al. (2005) Protein drug stability: a formulation challenge, Nature Reviews Drug Discovery, vol. 4, pp. 298-306.
Gainza et al. (2012) "Protein design using continuous rotamers" PLoS Computational Biology, 8(1), e1002335.
Goldstein (1994) "Efficient Rotamer Elimination Applied to Protein Side-Chains and Related Spin Glasses", Biophysical Journal, vol. 66, May 1994, pp. 1335-1340.
Gonzales et al. (2004) "SDR grafting of a murine antibody using multiple human germline templates to minimize its immunogenicity", Molecular Immunology, 41, 863-872.
Harding et al. (2010) "The immunogenicity of humanized and fully human antibodies. Residual immunogenicity resides in the CDR regions", mAbs, 2:3, pp. 256-265.
He L. et al.(2012) "A divide-and-conquer approach to determine the Pareto frontier for optimization of protein engineering experiments", Proteins: Structure, Function, and Bioinformatics, 80, 790-806.
Hermeling et al. (2004) "Structure-immunogenicity relationships of therapeutic proteins", Pharmaceutical Research, 21, pp. 897-903.
Hwang et al. (2005) "Immunogenicity of engineered antibodies", Methods, vol. 36, pp. 3-10.
International Search Report and Written Opinion in related PCT Application No. PCT/US2017/034175, dated Nov. 30, 2017 (16 pages).
International Preliminary Report on Patentability in related PCT Application No. PCT/US2017/034175, dated Nov. 27, 2018 (11 pages).
Jarasch et al. (2015) "Developability Assessment During the Selection of Novel Therapeutic Antibodies", Journal of Pharmaceutical Sciences, vol. 104, pp. 1885-1898.
Jawa et al. (2013) "T-cell dependent immunogenicity of protein therapeutics: preclinical assessment and mitigation", Clinical Immunology, vol. 149, pp. 534-555.
Jones et al. (1986) "Replacing the complementarity-determining regions in a human antibody with those from a mouse", Nature, 321, pp. 522-525.
Khee et al. (2005) "Use of human germline genes in a CDR homology-based approach to antibody humanization", Methods, vol. 36, pp. 35-42.
Kirkpatrick et al. (2004) "Cetuximab", Nature Reviews Drug Discovery, 3, pp. 549-550.
Lazar et al. (2007) "A molecular immunology approach to antibody humanization and functional optimization", Molecular Immunology, 44, pp. 1986-1998.
Lee et al. (2014) "Complete humanization of the mouse immunoglobulin loci enables efficient therapeutic antibody discovery", Nature Biotechnology, vol. 32, No. 4, pp. 356-363.
Li et al. (2006) "Human antibodies for immunotherapy development generated via a human B cell hybridoma technology", Proceedings of the National Academy of Sciences of the United States of America, vol. 103, No. 10, pp. 3557-3562.
Lonberg N. (2008), Human Monoclonal Antibodies from Transgenic Mice"\, Therapeutic Antibodies", Springer-Verlag, pp. 69-97.
Lovell et al., The penultimate rotamer library. Proteins Jun. 12, 2000, vol. 40, Issue 3, pp. 389-408.
Lu et al. (2012) "Frontier of therapeutic antibody discovery: the challenges and how to face them", World Journal of Biological Chemistry, vol. 3, Issue 12, pp. 187-196.
McCafferty et al. (1990) "Phage antibodies: filamentous phage displaying antibody variable domains", Nature, vol. 348, pp. 552-554.
McConnell et al. (2013) "An integrated approach to extreme thermostabilization and affinity maturation of an antibody", Protein Engineering Design and Selection, vol. 26, pp. 151-164.
Nelson et al. (2010) "Development trends for human monoclonal antibody therapeutics", Nature reviews Drug Discovery, vol. 9, pp. 767-774.
Niesen et al. (2007) "The use of differential scanning fluorimetry to detect ligand interactions that promote protein stability", Nature Protocols, vol. 2, pp. 2212-2221.
Osbourn et al. (2005) "From rodent reagents to human therapeutics using antibody guided selection", Methods, vol. 36, pp. 61-68.
Padlan, "A possible procedure for reducing the immunogenicity of antibody variable domains while preserving their ligand-binding properties", 1991, Molecular Immunology vol. 28, Issues 4-5, pp. 489-498.
Parham et al., "Population biology of antigen presentation by MHC class I molecules", Science 1996, vol. 272, Issue 5258, pp. 67-74.
Parker et al. (2013) "Structure-guided deimmunization of therapeutic proteins", Journal of Computational Biology, vol. 20, pp. 152-165.
Parker et al. (2010) "Optimization algorithms for functional deimmunization of therapeutic proteins", BMC Bioinformatics, 11:180.
Pearlman et al. (1995) "AMBER, a package of computer programs for applying molecular mechanics, normal mode analysis, molecular dynamics and free energy calculations to simulate the structural and energetic properties of molecules", Computer Physics Communications, 91, pp. 1-41.
Pedersen et al. (1994) "Comparison of surface accessible residues in human and murine immunoglobulin Fv domains: implication for humanization of murine antibodies", Journal of Molecular Biology, 235, pp. 959-973.
Pendley et al. (2003) "Immunogenicity of therapeutic monoclonal antibodies", Current Opinion in Molecular Therapeutics, 5, pp. 172-179.
Poiron et al. (2010) "IMGT/mAb-DB: the IMGT database for therapeutic monoclonal antibodies", JOBIM, Paper 13.

(56) References Cited

OTHER PUBLICATIONS

Qiu et al. (1997) "The GB/SA continuum model for solvation. A fast analytical method for the calculation of approximate born radii", The Journal of Physical Chemistry A, 101, pp. 3005-3014.
Ratanji et al. (2014) "Immunogenicity of therapeutic proteins: Influence of aggregation", Journal of Immunotoxicology, 11(2) pp. 99-109.
Reche et al. "Sequence variability analysis of human class I and class II MHC molecules: functional and structural correlates of amino acid polymorphisms", Journal of Molecular Biology, Aug. 15, 2003, vol. 331, Issue 3, pp. 623-641.
Retter et al. (2005) "VBASE2, an integrative V gene database", Nucleic Acids Research, vol. 33, D671-D674.
Roguska et al. (1994) "Humanization of murine monoclonal antibodies through variable domain resurfacing", Proceedings of the National Academy of Sciences, vol. 91, pp. 969-973.
Rosenberg A.S. (2006) "Effects of protein aggregates: an immunologic perspective", The AAPS Journal, 8, E501-E507.
Roskos et al. (2004) "The clinical pharmacology of therapeutic monoclonal antibodies", Drug Development Research, vol. 61, pp. 108-120.
Röthlisberger et al. (2005) "Domain interactions in the Fab fragment: a comparative evaluation of the single-chain Fv and Fab format engineered with variable domains of different stability", Journal of Molecular Biology, vol. 347, pp. 773-789.
Schellekens H. (2002) "Immunogenicity of therapeutic proteins: clinical implications and future prospects", Clinical Therapeutics, vol. 24, pp. 1720-1740.
Studnicka et al. (1994) "Human-engineered monoclonal antibodies retain full specific binding activity by preserving non-CDR complementarity-modulating residues", Protein Engineering, 7(6), pp. 805-814.
Swann et al. (2008) "Considerations for the development of therapeutic monoclonal antibodies", Current Opinion in Immunology, vol. 20, pp. 493-499.
Wiens et al. (1998) "Harmful somatic mutations: lessons from the dark side", Immunological Reviews, vol. 162, pp. 197-209.

* cited by examiner

Fig. 9

Design (VH)

| Chothia | 5 | 6 | 9 | 12 | 13 | 16 | 17 | 20 | 40 | 58 | 61 | 63 | 64 | 68 | 70 | 71 | 72A | 73 | 76 | 77 | 79 | 80 | 82 | 83 | 84 | 85 | 89 | Difference (Cetuximab) | Difference (Germline) |
|---|---|---|---|---|---|---|---|---|---|---|---|---|---|---|---|---|---|---|---|---|---|---|---|---|---|---|---|---|---|
| Kabat | 5 | 6 | 9 | 12 | 13 | 16 | 17 | 20 | 40 | 58 | 61 | 63 | 64 | 68 | 70 | 71 | 73 | 76 | 79 | 80 | 82 | 82A | 82C | 83 | 84 | 85 | 89 | | |
| **Cetuximab** | **K** | **Q** | **P** | **V** | **Q** | **Q** | **S** | **I** | **S** | **D** | **T** | **F** | **T** | **S** | **N** | **K** | **N** | **S** | **F** | **F** | **M** | **N** | **L** | **Q** | **S** | **N** | **I** | | |
| **C1** | Q | | | | K | | T | L | | | | | | T | S | | T | N | S | L | L | S | V | T | | | V | 17 | 8 |
| **C2** | Q | | | | K | | T | L | | | | | | T | S | V | T | N | S | L | L | S | V | T | | | V | 16 | 7 |
| **C3** | Q | | | | K | E | T | L | | | | | | T | S | V | T | N | S | L | L | S | V | T | | | V | 17 | 7 |
| **C4** | Q | | | | K | | T | L | | | | | | T | S | | | | | | | | | | | | V | 7 | 15 |
| **C5** | Q | | | | K | E | T | | | | | | | T | | | | | | | | | | | | | V | 6 | 17 |
| **G1** | Q | | | | K | | T | | P | | | | | T | S | | | | S | | | S | | T | A | A | | 11 | 12 |
| **G2** | Q | | A | L | K | E | T | | P | *N* | *P* | *L* | *K* | T | S | | T | N | S | | | S | | T | A | A | V | 21 | 9 |
| **G3** | Q | E | A | L | K | E | T | | P | | | | | T | S | | T | N | S | | L | S | V | T | A | A | V | 20 | 7 |
| **G4** | Q | E | | | K | | T | | P | | | | | T | S | | | | S | | L | S | V | T | A | A | | 14 | 10 |

Design (Vκ)

| Chothia | 1 | 3 | 9 | 10 | 11 | 14 | 16 | 18 | 20 | 21 | 22 | 34 | 39 | 40 | 41 | 42 | 43 | 45 | 58 | 74 | 83 | Difference (Cetuximab) | Difference (Germline) |
|---|---|---|---|---|---|---|---|---|---|---|---|---|---|---|---|---|---|---|---|---|---|---|---|
| Kabat | 1 | 3 | 9 | 10 | 11 | 14 | 16 | 18 | 20 | 21 | 22 | 34 | 39 | 40 | 41 | 42 | 43 | 45 | 58 | 74 | 83 | | |
| **Cetuximab** | **D** | **L** | **V** | **I** | **L** | **S** | **G** | **R** | **S** | **F** | **S** | **H** | **R** | **T** | **N** | **G** | **S** | **R** | **I** | **S** | **I** | | |
| **C1** | | V | D | F | Q | G | K | K | T | | | | K | P | D | Q | | K | V | T | | 15 | 6 |
| **C2** | | V | | F | | G | | K | T | | | | K | P | D | Q | | K | V | T | | 14 | 9 |
| **C3** | | | | | | | | | T | | | | K | P | D | Q | | K | V | T | | 8 | 15 |
| **C4** | | V | | | | | | | T | | | | K | P | D | Q | | K | V | T | | 9 | 14 |
| **C5** | E | V | | | | | | | T | | | | K | | D | Q | | | | T | | 7 | 16 |
| **G1** | E | V | D | F | Q | T | K | K | T | F | T | | K | | | Q | | | | T | A | 14 | 10 |
| **G2** | E | V | D | F | | T | K | K | T | F | T | | K | | | | | | | T | A | 12 | 12 |
| **G3** | | V | A | F | | T | | K | T | F | T | | K | | | Q | A | | | T | A | 12 | 15 |
| **G4** | E | V | D | F | Q | T | K | K | T | F | T | Y | K | P | D | Q | | | | T | A | 17 | 9 |

Fig. 10

| | | Replicate 1 | | | | Replicate 2 | | | |
|---|---|---|---|---|---|---|---|---|---|
| VH | Vκ | $T_M^{10}$ | $T_M^{20}$ | $T_M^{50}$ | $T_M^{100}$ | $T_M^{10}$ | $T_M^{20}$ | $T_M^{50}$ | $T_M^{100}$ |
| Cetuximab | Cetuximab | 69.6 | 69.6 | 69.6 | 69.6 | 69.1 | 69.1 | 69.1 | 69.1 |
| C1 | C1 | 72.9 | 72.9 | 72.9 | 72.9 | 73.2 | 73.2 | 73.2 | 73.2 |
| C1 | C2 | 75.2 | 75.2 | 75.2 | 75.2 | 75.2 | 75.2 | 75.2 | 75.2 |
| C1 | C3 | 63.7 | 63.7 | 63.7 | 64.1 | 58.7 | 58.7 | 58.7 | 58.8 |
| C1 | C4 | 74.9 | 74.9 | 74.9 | 74.9 | 74.9 | 74.9 | 74.9 | 74.9 |
| C1 | C5 | 74.6 | 74.6 | 74.6 | 74.7 | 75.0 | 75.0 | 75.0 | 75.0 |
| C2 | C1 | 71.6 | 71.6 | 71.6 | 71.7 | 71.6 | 71.6 | 71.6 | 71.6 |
| C2 | C2 | 73.5 | 73.5 | 73.5 | 73.5 | 73.3 | 73.3 | 73.3 | 73.3 |
| C2 | C3 | N. D. | N. D. | N. D. | N. D. | N. D. | N. D. | N. D. | N. D. |
| C2 | C4 | 73.4 | 73.4 | 73.4 | 73.5 | 73.1 | 73.1 | 73.1 | 73.1 |
| C2 | C5 | 73.5 | 73.5 | 73.5 | 73.5 | 73.6 | 73.6 | 73.6 | 73.7 |
| C3 | C1 | 72.2 | 72.2 | 72.2 | 72.2 | 72.1 | 72.1 | 72.1 | 72.1 |
| C3 | C2 | 74.8 | 74.8 | 74.8 | 74.8 | 74.5 | 74.5 | 74.5 | 74.5 |
| C3 | C3 | 72.6 | 72.6 | 72.6 | 72.7 | 72.1 | 72.1 | 72.1 | 72.1 |
| C3 | C4 | 70.3 | 70.3 | 70.3 | 70.3 | 70.4 | 70.4 | 70.4 | 70.5 |
| C3 | C5 | 69.5 | 69.5 | 69.5 | 69.5 | 66.1 | 66.1 | 66.1 | 66.1 |
| C4 | C1 | 71.9 | 71.9 | 71.9 | 71.9 | 71.6 | 71.6 | 71.6 | 71.6 |
| C4 | C2 | 73.2 | 73.2 | 73.2 | 73.2 | 72.8 | 72.8 | 72.8 | 72.9 |
| C4 | C3 | 72.0 | 72.0 | 72.0 | 72.1 | 72.0 | 72.0 | 72.0 | 72.0 |
| C4 | C4 | 73.2 | 73.2 | 73.2 | 73.2 | 73.5 | 73.5 | 73.5 | 73.5 |
| C4 | C5 | 73.9 | 73.9 | 73.9 | 73.9 | 73.7 | 73.7 | 73.7 | 73.7 |
| C5 | C1 | 71.5 | 71.5 | 71.5 | 71.5 | 71.2 | 71.2 | 71.2 | 71.2 |
| C5 | C2 | 72.4 | 72.4 | 72.4 | 72.4 | 72.7 | 72.7 | 72.7 | 72.7 |
| C5 | C3 | 71.7 | 71.7 | 71.7 | 71.7 | 71.7 | 71.7 | 71.7 | 71.8 |
| C5 | C4 | 72.8 | 72.8 | 72.8 | 72.9 | 72.8 | 72.8 | 72.8 | 72.8 |
| C5 | C5 | 72.6 | 72.6 | 72.6 | 72.6 | 72.2 | 72.2 | 72.2 | 72.2 |
| G1 | G1 | 45.2 | 66.2 | 66.2 | 66.2 | 66.5 | 66.5 | 66.5 | 66.5 |
| G1 | G2 | 46.5 | 65.2 | 65.2 | 65.3 | 46.9 | 65.7 | 65.7 | 66.1 |
| G1 | G3 | 50.5 | 67.2 | 67.2 | 68.7 | 48.8 | 67.5 | 67.5 | 69.8 |
| G1 | G4 | 66.7 | 66.7 | 66.7 | 69.3 | 66.9 | 66.9 | 66.9 | 69.3 |
| G2 | G1 | 58.0 | 60.2 | 81.4 | 81.4 | 57.9 | 60.4 | 81.3 | 81.3 |
| G2 | G2 | 48.0 | 82.4 | 82.4 | 82.5 | 48.5 | 82.8 | 82.8 | 82.8 |
| G2 | G3 | 52.4 | 52.4 | 64.4 | 64.9 | 52.4 | 52.4 | 64.6 | 65.0 |
| G2 | G4 | 58.5 | 60.1 | 81.3 | 81.3 | 58.5 | 60.3 | 81.4 | 81.4 |
| G3 | G1 | 63.9 | 63.9 | 70.8 | 70.8 | 63.9 | 63.9 | 70.9 | 70.9 |
| G3 | G2 | 47.8 | 63.8 | 63.8 | 69.1 | 47.5 | 64.0 | 64.0 | 69.3 |
| G3 | G3 | 48.4 | 48.4 | 65.8 | 66.1 | 46.7 | 46.7 | 65.8 | 66.0 |
| G3 | G4 | 63.8 | 63.8 | 76.8 | 77.0 | 63.9 | 63.9 | 77.3 | 77.3 |
| G4 | G1 | 69.8 | 69.8 | 80.3 | 80.3 | 69.8 | 69.8 | 80.6 | 80.6 |
| G4 | G2 | 69.6 | 69.6 | 80.1 | 80.2 | 69.7 | 69.7 | 80.3 | 80.3 |
| G4 | G3 | 50.8 | 50.8 | 69.9 | 69.9 | 50.5 | 50.5 | 69.7 | 69.7 |
| G4 | G4 | 69.8 | 69.8 | 81.3 | 81.3 | 69.9 | 69.9 | 81.1 | 81.1 |

ANTIBODIES AND METHODS OF MAKING SAME

RELATED APPLICATIONS

This application is a 35 U.S.C. 371 filing of International Application No. PCT/US2017/034175, filed May 24, 2017, which application claims the benefit of U.S. provisional patent application No. 62/340,985, filed May 24, 2016, the contents of which is incorporated herein by reference in its entirety.

GOVERNMENT SUPPORT

This invention was made with government support under R01 GM098977 awarded by National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Apr. 23, 2021, is named 607229KGT-002US_SL.txt and is 24.0 bytes in size.

FIELD OF THE INVENTION

This invention relates to antibodies, methods of predicting the sequences of variant antibodies, and methods of making same. The invention relates more particularly to variant antibodies to human epidermal growth factor receptor (EGFR).

BACKGROUND OF THE INVENTION

Antibodies have emerged as a leading class of biotherapeutics (Aggarwal, 2014), but despite a long history and large market presence, developers of new antibodies continue to face a number of challenges (Lu et al., 2012). One such issue is immunogenicity risk, wherein anti-biotherapeutic antibody responses can reduce therapeutic efficacy and manifest a range of other detrimental side effects (Jawa et al., 2013, Pendley et al., 2003, Roskos et al., 2004, Schellekens, 2002, Swann et al., 2008). This issue has been in part, though not entirely (Harding et al., 2010, Hwang and Foote, 2005), addressed by the establishment of well-defined humanization methods (Baca et al., 1997, Dall'Acqua et al., 2005, Dennis, 2010, Gonzales et al., 2004, Jones et al., 1986, Khee Hwang et al., 2005, Lazar et al., 2007, Osbourn et al., 2005, Roguska et al., 1994) and the advent of "fully human" antibodies (Duvall et al., 2011, Feldhaus et al., 2003, Lee et al., 2014, Li et al., 2006, Lonberg, 2008, McCafferty et al., 1990). Stability is another determinant of therapeutic antibody "developability" (Jarasch et al., 2015), as loss of structural integrity can degrade binding activity, cause aggregation, and generally undermine therapeutic potential (Frokjaer and Otzen, 2005, Hermeling et al., 2004). Biotherapeutic aggregation and immunogenicity are often correlated, as protein aggregates, resulting from poor thermostability or other factors, can exacerbate classical anti-drug antibody responses and produce detrimental responses via non-classical pathways (Ratanji et al., 2013, Rosenberg, 2006).

Despite accelerating growth in fully human antibody technologies, immunization of animal models followed by antibody cloning and humanization is simple, convenient, and widely used (Nelson et al., 2010). Humanization via complementarity determining region (CDR) grafting is a common strategy. Unfortunately, CDR grafting often leads to considerable decreases in thermostability and binding affinity, requiring back substitution of non-human residues to mitigate loss of functionality (Clark, 2000). Thus successful engineering of humanized antibodies requires simultaneous consideration of multiple objectives: humanness, thermostabililty, and binding affinity.

SUMMARY OF THE INVENTION

The invention is based in part on the development of variant cetuximab sequences. Variants within the invention show enhanced thermostability (up to a 6° C. higher melting point) and substantially improved humanness, i.e., they resemble more closely the germline form of the heavy chain and/or light chain gene than a starting, or parent, cetuximab antibody. In addition, binding affinities are near to or even better than that of the parental antibody (up to 1.5 times superior $K_D$).

In one aspect, the invention provides an isolated variant cetuximab antibody monoclonal antibody or antigen binding portion thereof. The antibody or antigen binding fragment includes a heavy chain and/or a light chain. The heavy chain and/or light chain is more similar in sequence to a germ-line EGFR antibody sequence than is a counterpart cetuximamb polypeptide, e.g., a polypeptide comprising SEQ ID NO:1 or SEQ ID NO:2.

In another aspect, the invention provides an isolated monoclonal antibody or antigen binding portion thereof. The antibody or antigen-binding portion thereof, the antibody or antigen binding fragment comprising a heavy chain and a light chain that is more thermostable than the corresponding isolated monoclonal antibody or antigen binding portion thereof comprising SEQ ID NO:1 and SEQ ID NO:2.

In a further aspect, the invention provides an isolated monoclonal antibody or antigen binding portion thereof that heavy chain and/or light chain is both more more similar in sequence to a germ-line EGFR antibody sequence than is a counterpart polypeptide comprising SEQ ID NO:1 or SEQ ID NO:2 and is also more thermostable than the corresponding isolated monoclonal antibody or antigen binding portion thereof comprising SEQ ID NO:1 and SEQ ID NO:2.

In some embodiments, the heavy chain or light chain is more similar in sequence to a germ-line EGFR antibody sequences, e.g., a germ line antibody sequence selected from the group consisting of SEQ ID NOs.:19-22 and 23, than is SEQ ID NO:1 or SEQ ID NO:2. In some embodiments, the heavy or light chain sequence comprises the sequences disclosed in Table 1.

In some embodiments, the isolated monoclonal antibody further comprises a heavy chain CDR1 (HCDR1) region selected from the group consisting of SEQ ID NO:13, SEQ ID NO: 14 and SEQ ID NO:15.

In some embodiments, the isolated monoclonal antibody further comprises a light chain CDR1 (LCDR1) region selected from the group consisting of SEQ ID NO:16, SEQ ID NO: 17 and SEQ ID NO:18.

In a still further aspect, the invention provides an isolated nucleic acid sequence encoding a variant cetuximab monoclonal antibody. The nucleic acid sequence may encode a heavy chain antibody, a light chain antibody, or both.

Also provided by the invention is a recombinant expression vector that includes an isolated nucleic acid sequence encoding a variant cetuximab monoclonal antibody.

In another aspect the invention includes a recombinant expression host cell that includes a nucleic acid sequence encoding a variant cetuximab monoclonal antibody, e.g., a recombinant expression vector with a variant cetuximab monoclonal antibody encoding sequence. A host cell may include nucleic acid sequences encoding heavy chain variant cetuximab polypeptides, nucleic acid sequences encoding light chain variant cetuximab polypeptides, or both heavy chain and light chain variant cetuximab polypeptides.

In a further aspect, the invention provides a pharmaceutical composition comprising a variant cetuximab antibody, or antigen-binding portion thereof, and a pharmaceutically acceptable carrier.

In a still further aspect, the invention provides a method of treating an EGFR-associated disease or disorder. The method includes administering an effective amount of a pharmaceutical composition comprising a variant cetuximab antibody, or antigen-binding portion thereof, to a patient in need thereof.

In some embodiments, the EGFR-associated disease or disorder is a cancer or tumor expressing EGFR. The cancer or tumor can be, e.g., glioblastoma, ductal or intraductal breast carcinoma, non-small squamous cell carcinoma, ovarian carcinoma, prostate cancer, or squamous cell carcinoma of the head and neck.

In some embodiments, the disease or disorder is an inflammatory or autoimmune disease or disorder, e.g., chronic obstructive pulmonary disease, systemic lupus erythematosus, rheumatoid arthritis, splanchnic artery occlusion shock, spinal cord injury, type 1 diabetes, or multiple sclerosis.

In some embodiments, t the pharmaceutical composition is administered in combination with one or more additional therapeutic agents. The additional therapeutic agent can be, e.g., IL-18 antagonist, IL-12 antagonist, TNF antagonist, methotrexate, corticosteroid, cyclosporin, rapamycin, FK506, and/or non-steroidal anti-inflammatory agents.

The additional agent or agents can be administered either concurrently with the variant cetuximab antibody pharmaceutical composition or at a separate time.

Also provided by the invention is a method making a variant cetuximab antibody. The method includes culturing a cell under conditions that allow for expression and function of a variant cetuximab antibody. In some embodiments, the method includes purifying the expressed variant cetuximab antibody.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF DRAWINGS

FIG. 2. CoDAH designs.

FIG. 6A is CoDAH replicate 1. FIG. 6B is CoDAH replicate 2. FIG. 6C is CDR grafted replicate 1. FIG. 6D is CDR grafted replicate 2. The last column and row are combined curves. The curve of C3 VK/C2 VH was not determined and is omitted. Vertical dark lines indicate TM20* values.

FIG. 9. Mutations made in each humanized design (C: CoDAH, G: Grafted). The last two columns are positional differences between cetuximab and closest human antibody germline sequences (excluding CDRs). For CDR-grafted designs, knowledge-based restrictions were imposed. For G2 VH, some mutations were introduced at non-overlapping positions in CDR-H2 by the Kabat and Chothia numbering schemes (underlined italic). The cetuximab sequence under the "Design (VH)" section of FIG. 9 corresponds to SEQ ID NO: 34 and the cetuximab sequence under the "Design (Vκ)" section of FIG. 9 corresponds to SEQ ID NO: 35.

FIG. 10. TM*values computed for different minimum transition cutoffs. TM 100* indicates the midpoint between the maximum and minimum intensities. TM10*, TM20*, and TM50* indicate the midpoint between the maximum intensity and first local minimum exceeding respectively 10%, 20%, or 50%. If a melting curve has a single transition, these all exhibit identical values. Colored shading indicates designs exhibiting two (light grey) or more (dark grey) distinct melting transitions. Raw melting curves of TM20* are shown in FIG. 6A-D.

DETAILED DESCRIPTION OF INVENTION

Figure 1:
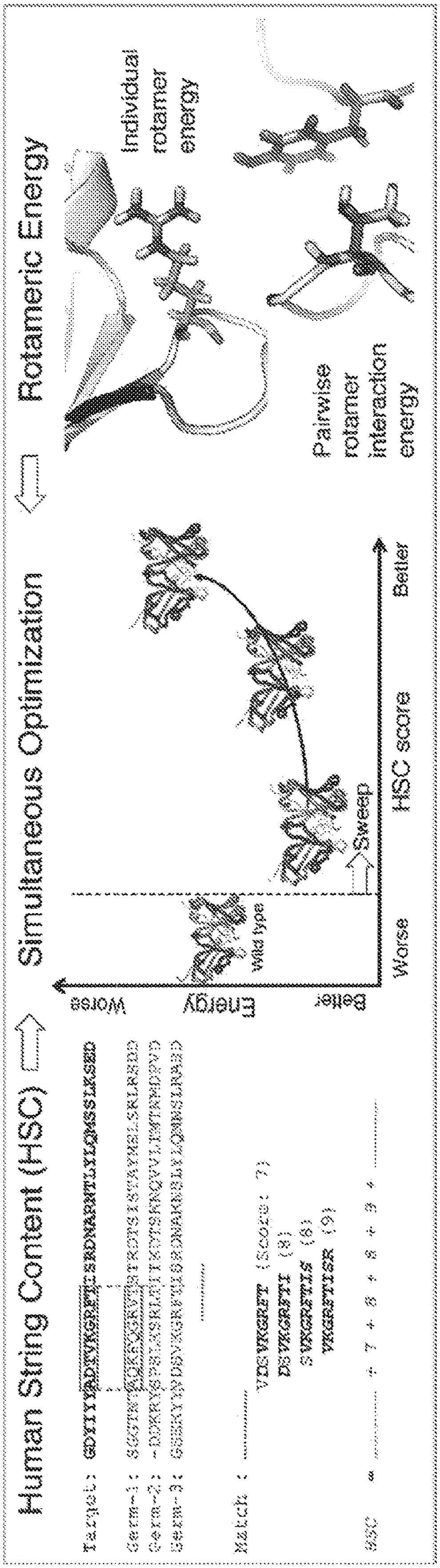
FIG. 1. Overview of the structure-based antibody humanization method. (left) Humanness is evaluated by the human string content (HSC) score which calculates aligned nonamer matches against human antibody germline sequences. (right) Structural stability is evaluated by rotameric energy, comprised of position-specific terms for rotamers at individual positions (side-chain internal energy plus backbone interaction) and pairs of positions (side-chain interactions). (center) Sets of mutations are chosen so as to make optimal trade-offs between the competing humanness and energy scores. Fab structures are dark colored for higher HSC. Sequences displayed from top to bottom correspond to SEQ ID NOs: 24-31.

We applied CoDAH to engineer variants of cetuximab, a chimeric antibody targeting the epidermal growth factor receptor (EGFR) (Kirkpatrick et al., 2004). The computationally designed variants consistently exhibit enhanced thermostabilities (up to 6° C.) and substantially improved humanness, along with binding affinities near to or even better than that of the parental antibody (up to 1.5 times better KD).

Antibodies

The term "antibody" is used herein in the broadest sense and specifically covers monoclonal antibodies (including full length monoclonal antibodies) of any isotype such as IgG, IgM, IgA, IgD and IgE, polyclonal antibodies, multispecific antibodies, chimeric antibodies, and antibody fragments. An antibody reactive with a specific antigen can be generated by recombinant methods such as selection of libraries of recombinant antibodies in phage or similar vectors, or by immunizing an animal with the antigen or an antigen-encoding nucleic acid.

A typical IgG antibody is comprised of two identical heavy chains and two identical light chains that are joined by disulfide bonds. Each heavy and light chain contains a constant region and a variable region. Each variable region contains three segments called "complementarity-determining regions" ("CDRs") or "hypervariable regions", which are primarily responsible for binding an epitope of an antigen. They are usually referred to as CDR1, CDR2, and CDR3, numbered sequentially from the N-terminus. The more highly conserved portions of the variable regions are called the "framework regions".

As used herein, "VH" or "VH" refers to the variable region of an immunoglobulin heavy chain of an antibody, including the heavy chain of an Fv, scFv, dsFv, Fab, Fab' or F(ab')2 fragment. Reference to "VL" or "VL" refers to the variable region of the immunoglobulin light chain of an antibody, including the light chain of an Fv, scFv, dsFv, Fab, Fab' or F(ab')2 fragment.

A "polyclonal antibody" is an antibody which was produced among or in the presence of one or more other, non-identical antibodies. In general, polyclonal antibodies are produced from a B-lymphocyte in the presence of several other B-lymphocytes producing non-identical antibodies. Usually, polyclonal antibodies are obtained directly from an immunized animal.

A "monoclonal antibody", as used herein, is an antibody obtained from a population of substantially homogeneous antibodies, i.e. the antibodies forming this population are essentially identical except for possible naturally occurring mutations which might be present in minor amounts. These antibodies are directed against a single epitope and are therefore highly specific.

An "epitope" is the site on the antigen to which an antibody binds. If the antigen is a polymer, such as a protein or polysaccharide, the epitope can be formed by contiguous residues or by non-contiguous residues brought into close proximity by the folding of an antigenic polymer. In proteins, epitopes formed by contiguous amino acids are typically retained on exposure to denaturing solvents, whereas epitopes formed by non-contiguous amino acids are typically lost under said exposure.

The "humanness" of an antibody is the degree to which it retains the sequence of a germ-line heavy chain or light chain counterpart antibody.

The term "humanized antibody", as used herein, refers to a chimeric antibody which contains minimal sequence derived from non-human immunoglobulin. The goal of humanization is a reduction in the immunogenicity of a xenogeneic antibody, such as a murine antibody, for introduction into a human, while maintaining the full antigen binding affinity and specificity of the antibody. Humanized antibodies, or antibodies adapted for non-rejection by other mammals, may be produced using several technologies such as resurfacing and CDR grafting. As used herein, the resurfacing technology uses a combination of molecular modeling, statistical analysis and mutagenesis to alter the non-CDR surfaces of antibody variable regions to resemble the surfaces of known antibodies of the target host. The CDR grafting technology typically involves substituting the complementarity determining regions of, for example, a mouse antibody, into a human framework domain, e.g., see WO 92/22653. Humanized chimeric antibodies preferably have constant regions and variable regions other than the complementarity determining regions (CDRS) derived substantially or exclusively from the corresponding human antibody regions and CDRs derived substantially or exclusively from a mammal other than a human.

Strategies and methods for the resurfacing of antibodies, and other methods for reducing immunogenicity of antibodies within a different host, are disclosed in U.S. Pat. No. 5,639,641, which is hereby incorporated in its entirety by reference. Briefly, in a preferred method, (1) position alignments of a pool of antibody heavy and light chain variable regions is generated to give a set of heavy and light chain variable region framework surface exposed positions wherein the alignment positions for all variable regions are at least about 98% identical; (2) a set of heavy and light chain variable region framework surface exposed amino acid residues is defined for a rodent antibody (or fragment thereof); (3) a set of heavy and light chain variable region framework surface exposed amino acid residues that is most closely identical to the set of rodent surface exposed amino acid residues is identified; (4) the set of heavy and light chain variable region framework surface exposed amino acid residues defined in step (2) is substituted with the set of heavy and light chain variable region framework surface exposed amino acid residues identified in step (3), except for those amino acid residues that are within 5 .ANG. of any atom of any residue of the complementarity-determining regions of the rodent antibody; and (5) the humanized rodent antibody having binding specificity is produced.

Antibodies can be humanized using a variety of other techniques including CDR-grafting (EP 0 239 400; WO 91/09967; U.S. Pat. Nos. 5,530,101; and 5,585,089), veneering or resurfacing (EP 0 592 106; EP 0 519 596; Padlan E. A., 1991, Molecular Immunology 28(415): 489-498; Studnicka G. M. et al., 1994, Protein Engineering, 7(6): 805-814; Roguska M. A. et al., 1994, PNAS, 91: 969-973), and chain shuffling (U.S. Pat. No. 5,565,332). Human antibodies can be made by a variety of methods known in the art including phage display methods. See also U.S. Pat. Nos. 4,444,887, 4,716,111, 5,545,806, and 5,814,318; and international patent application publication numbers WO 98/46645, WO 98/50433, WO 98/24893, WO 98/16654, WO 96/34096, WO 96/33735, and WO 91/10741 (said references incorporated by reference in their entireties).

Variant Cetuximab Molecules

Variant cetiuximab molecules according to the invention are shown below. Heavy chain cetuximab variants correspond to SEQ ID Nos: 3-7. Light chain cetuximab variants correspond to SEQ ID Nos: 8-12. Previously described cetuximab heavy chain and light sequences are shown as SEQ ID Nos. 1 and 2, respectively. As is shown below, the heavy and light chain variants are interchangeable.

| # | sequence (heavy) | sequence (light) |
|---|---|---|
| 1 | QVQLKQSGPGLVQPSQSLSITCTVSGFSLTNYG<br>VHWVRQSPGKGLEWLGVIWSGGNTDYNTPFT<br>SRLSINKDNSKSQVFFKMNSLQSNDTAIYYCAR<br>ALTYYDYEFAYWGQGTLVTVSA (SEQ ID NO:<br>1) | DILLTQSPVILSVSPGERVSFSCRASQSIGTNIHWYQ<br>QRTNGSPRLLIKYASESISGIPSRFSGSGSGTDFTLSI<br>NSVESEDIADYYCQQNNNWPTTFGAGTKLELKRT<br>V (SEQ ID NO: 2) |
| 2 | QVQLQQSGPGLVKPSQTLSLTCTVSGFSLTNYG<br>VHWVRQSPGKGLEWLGVIWSGGNTDYNTPFT<br>SRLTISKDTSKNQVSLKLSSVTSNDTAVYYCARA<br>LTYYDYEFAYWGQGTLVTVSA (SEQ ID NO: 3) | DIVLTQSPDFQSVTPKEKVTITCRASQSIGTNIHWY<br>QQKPDQSPKLLIKYASESISGVPSRFSGSGSGTDFTL<br>TINSVESEDIADYYCQQNNNWPTTFGAGTKLELKR<br>TV (SEQ ID NO: 8) |
| 3 | QVQLQQSGPGLVKPSQTLSLTCTVSGFSLTNYG<br>VHWVRQSPGKGLEWLGVIWSGGNTDYNTPFT<br>SRLTISKDTSKNQVSLKLSSVTSNDTAVYYCARA<br>LTYYDYEFAYWGQGTLVTVSA (SEQ ID NO: 3) | DIVLTQSPVFLSVTPGEKVTITCRASQSIGTNIHWY<br>QQKPDQSPKLLIKYASESISGVPSRFSGSGSGTDFTL<br>TINSVESEDIADYYCQQNNNWPTTFGAGTKLELKR<br>TV(SEQ ID NO: 9) |
| 4 | QVQLQQSGPGLVKPSQTLSLTCTVSGFSLTNYG<br>VHWVRQSPGKGLEWLGVIWSGGNTDYNTPFT<br>SRLTISKDTSKNQVSLKLSSVTSNDTAVYYCARA<br>LTYYDYEFAYWGQGTLVTVSA (SEQ ID NO: 3) | DILLTQSPVILSVSPGERVTFSCRASQSIGTNIHWYQ<br>QKPDQSPKLLIKYASESISGVPSRFSGSGSGTDFTLTI<br>NSVESEDIADYYCQQNNNWPTTFGAGTKLELKRT<br>V (SEQ ID NO: 10) |
| 5 | QVQLQQSGPGLVKPSQTLSLTCTVSGFSLTNYG<br>VHWVRQSPGKGLEWLGVIWSGGNTDYNTPFT<br>SRLTISKDTSKNQVSLKLSSVTSNDTAVYYCARA<br>LTYYDYEFAYWGQGTLVTVSA (SEQ ID NO: 3) | DIVLTQSPVILSVSPGERVTFSCRASQSIGTNIHWYQ<br>QKPDQSPKLLIKYASESISGVPSRFSGSGSGTDFTLTI<br>NSVESEDIADYYCQQNNNWPTTFGQGTKLELKRT<br>V (SEQ ID NO: 11) |
| 6 | QVQLQQSGPGLVKPSQTLSLTCTVSGFSLTNYG<br>VHWVRQSPGKGLEWLGVIWSGGNTDYNTPFT<br>SRLTISKDTSKNQVSLKLSSVTSNDTAVYYCARA<br>LTYYDYEFAYWGQGTLVTVSA (SEQ ID NO: 3) | EIVLTQSPVILSVSPGERVTFSCRASQSIGTNIHWYQ<br>QKTDQSPRLLIKYASESISGIPSRFSGSGSGTDFTLTI<br>NSVESEDIADYYCQQNNNWPTTFGQGTKLELKRT<br>V (SEQ ID NO: 12) |
| 7 | QVQLQQSGPGLVKPSQTLSLTCTVSGFSLTNYG<br>VHWVRQSPGKGLEWLGVIWSGGNTDYNTPFT<br>SRLTISVDTSKNQVSLKLSSVTSNDTAVYYCARA<br>LTYYDYEFAYWGQGTLVTVSA (SEQ ID NO: 4) | DIVLTQSPDFQSVTPKEKVTITCRASQSIGTNIHWY<br>QQKPDQSPKLLIKYASESISGVPSRFSGSGSGTDFTL<br>TINSVESEDIADYYCQQNNNWPTTFGAGTKLELKR<br>TV (SEQ ID NO: 8) |
| 8 | QVQLQQSGPGLVKPSQTLSLTCTVSGFSLTNYG<br>VHWVRQSPGKGLEWLGVIWSGGNTDYNTPFT<br>SRLTISVDTSKNQVSLKLSSVTSNDTAVYYCARA<br>LTYYDYEFAYWGQGTLVTVSA (SEQ ID NO: 4) | DIVLTQSPVFLSVTPGEKVTITCRASQSIGTNIHWY<br>QQKPDQSPKLLIKYASESISGVPSRFSGSGSGTDFTL<br>TINSVESEDIADYYCQQNNNWPTTFGAGTKLELKR<br>TV (SEQ ID NO: 9) |
| 9 | QVQLQQSGPGLVKPSQTLSLTCTVSGFSLTNYG<br>VHWVRQSPGKGLEWLGVIWSGGNTDYNTPFT<br>SRLTISVDTSKNQVSLKLSSVTSNDTAVYYCARA<br>LTYYDYEFAYWGQGTLVTVSA (SEQ ID NO: 4) | DILLTQSPVILSVSPGERVTFSCRASQSIGTNIHWYQ<br>QKPDQSPKLLIKYASESISGVPSRFSGSGSGTDFTLTI<br>NSVESEDIADYYCQQNNNWPTTFGAGTKLELKRT<br>V (SEQ ID NO: 10) |
| 10 | QVQLQQSGPGLVKPSQTLSLTCTVSGFSLTNYG<br>VHWVRQSPGKGLEWLGVIWSGGNTDYNTPFT<br>SRLTISVDTSKNQVSLKLSSVTSNDTAVYYCARA<br>LTYYDYEFAYWGQGTLVTVSA (SEQ ID NO: 4) | DIVLTQSPVILSVSPGERVTFSCRASQSIGTNIHWYQ<br>QKPDQSPKLLIKYASESISGVPSRFSGSGSGTDFTLTI<br>NSVESEDIADYYCQQNNNWPTTFGQGTKLELKRT<br>V (SEQ ID NO: 11) |
| 11 | QVQLQQSGPGLVKPSQTLSLTCTVSGFSLTNYG<br>VHWVRQSPGKGLEWLGVIWSGGNTDYNTPFT<br>SRLTISVDTSKNQVSLKLSSVTSNDTAVYYCARA<br>LTYYDYEFAYWGQGTLVTVSA (SEQ ID NO: 4) | EIVLTQSPVILSVSPGERVTFSCRASQSIGTNIHWYQ<br>QKTDQSPRLLIKYASESISGIPSRFSGSGSGTDFTLTI<br>NSVESEDIADYYCQQNNNWPTTFGQGTKLELKRT<br>V (SEQ ID NO: 12) |

-continued

| # | sequence (heavy) | sequence (light) |
|---|---|---|
| 12 | QVQLQQSGPGLVKPSETLSLTCTVSGFSLTNYG<br>VHWVRQSPGKGLEWLGVIWSGGNTDYNTPFT<br>SRLTISVDTSKNQVSLKLSSVTSNDTAVYYCARA<br>LTYYDYEFAYWGQGTLVTVSA (SEQ ID NO: 5) | DIVLTQSPDFQSVTPKEKVTITCRASQSIGTNIHWY<br>QQKPDQSPKLLIKYASESISGVPSRFSGSGSGTDFTL<br>TINSVESEDIADYYCQQNNNWPTTFGAGTKLELKR<br>TV (SEQ ID NO: 8) |
| 13 | QVQLQQSGPGLVKPSETLSLTCTVSGFSLTNYG<br>VHWVRQSPGKGLEWLGVIWSGGNTDYNTPFT<br>SRLTISVDTSKNQVSLKLSSVTSNDTAVYYCARA<br>LTYYDYEFAYWGQGTLVTVSA (SEQ ID NO: 5) | DIVLTQSPVFLSVTPGEKVTITCRASQSIGTNIHWY<br>QQKPDQSPKLLIKYASESISGVPSRFSGSGSGTDFTL<br>TINSVESEDIADYYCQQNNNWPTTFGAGTKLELKR<br>TV (SEQ ID NO: 9) |
| 14 | QVQLQQSGPGLVKPSETLSLTCTVSGFSLTNYG<br>VHWVRQSPGKGLEWLGVIWSGGNTDYNTPFT<br>SRLTISVDTSKNQVSLKLSSVTSNDTAVYYCARA<br>LTYYDYEFAYWGQGTLVTVSA (SEQ ID NO: 5) | DILLTQSPVILSVSPGERVTFSCRASQSIGTNIHWYQ<br>QKPDQSPKLLIKYASESISGVPSRFSGSGSGTDFTLTI<br>NSVESEDIADYYCQQNNNWPTTFGAGTKLELKRT<br>V (SEQ ID NO: 10) |
| 15 | QVQLQQSGPGLVKPSETLSLTCTVSGFSLTNYG<br>VHWVRQSPGKGLEWLGVIWSGGNTDYNTPFT<br>SRLTISVDTSKNQVSLKLSSVTSNDTAVYYCARA<br>LTYYDYEFAYWGQGTLVTVSA (SEQ ID NO: 5) | DIVLTQSPVILSVSPGERVTFSCRASQSIGTNIHWYQ<br>QKPDQSPKLLIKYASESISGVPSRFSGSGSGTDFTLTI<br>NSVESEDIADYYCQQNNNWPTTFGQGTKLELKRT<br>V (SEQ ID NO: 11) |
| 16 | QVQLQQSGPGLVKPSETLSLTCTVSGFSLTNYG<br>VHWVRQSPGKGLEWLGVIWSGGNTDYNTPFT<br>SRLTISVDTSKNQVSLKLSSVTSNDTAVYYCARA<br>LTYYDYEFAYWGQGTLVTVSA (SEQ ID NO: 5) | EIVLTQSPVILSVSPGERVTFSCRASQSIGTNIHWYQ<br>QKTDQSPRLLIKYASESISGIPSRFSGSGSGTDFTLTI<br>NSVESEDIADYYCQQNNNWPTTFGQGTKLELKRT<br>V (SEQ ID NO: 12) |
| 17 | QVQLQQSGPGLVKPSQTLSLTCTVSGFSLTNYG<br>VHWVRQSPGKGLEWLGVIWSGGNTDYNTPFT<br>SRLTISKDNSKSQVFFKMNSLQSNDTAVYYCAR<br>ALTYYDYEFAYWGQGTLVTVSA (SEQ ID NO:<br>6) | DIVLTQSPDFQSVTPKEKVTITCRASQSIGTNIHWY<br>QQKPDQSPKLLIKYASESISGVPSRFSGSGSGTDFTL<br>TINSVESEDIADYYCQQNNNWPTTFGAGTKLELKR<br>TV (SEQ ID NO: 8) |
| 18 | QVQLQQSGPGLVKPSQTLSLTCTVSGFSLTNYG<br>VHWVRQSPGKGLEWLGVIWSGGNTDYNTPFT<br>SRLTISKDNSKSQVFFKMNSLQSNDTAVYYCAR<br>ALTYYDYEFAYWGQGTLVTVSA (SEQ ID NO:<br>6) | DIVLTQSPVFLSVTPGEKVTITCRASQSIGTNIHWY<br>QQKPDQSPKLLIKYASESISGVPSRFSGSGSGTDFTL<br>TINSVESEDIADYYCQQNNNWPTTFGAGTKLELKR<br>TV(SEQ ID NO: 9) |
| 19 | QVQLQQSGPGLVKPSQTLSLTCTVSGFSLTNYG<br>VHWVRQSPGKGLEWLGVIWSGGNTDYNTPFT<br>SRLTISKDNSKSQVFFKMNSLQSNDTAVYYCAR<br>ALTYYDYEFAYWGQGTLVTVSA (SEQ ID NO:<br>6) | DILLTQSPVILSVSPGERVTFSCRASQSIGTNIHWYQ<br>QKPDQSPKLLIKYASESISGVPSRFSGSGSGTDFTLTI<br>NSVESEDIADYYCQQNNNWPTTFGAGTKLELKRT<br>V (SEQ ID NO: 10) |
| 20 | QVQLQQSGPGLVKPSQTLSLTCTVSGFSLTNYG<br>VHWVRQSPGKGLEWLGVIWSGGNTDYNTPFT<br>SRLTISKDNSKSQVFFKMNSLQSNDTAVYYCAR<br>ALTYYDYEFAYWGQGTLVTVSA (SEQ ID NO:<br>6) | DIVLTQSPVILSVSPGERVTFSCRASQSIGTNIHWYQ<br>QKPDQSPKLLIKYASESISGVPSRFSGSGSGTDFTLTI<br>NSVESEDIADYYCQQNNNWPTTFGQGTKLELKRT<br>V (SEQ ID NO: 11) |
| 21 | QVQLQQSGPGLVKPSQTLSLTCTVSGFSLTNYG<br>VHWVRQSPGKGLEWLGVIWSGGNTDYNTPFT<br>SRLTISKDNSKSQVFFKMNSLQSNDTAVYYCAR<br>ALTYYDYEFAYWGQGTLVTVSA (SEQ ID NO:<br>6) | EIVLTQSPVILSVSPGERVTFSCRASQSIGTNIHWYQ<br>QKTDQSPRLLIKYASESISGIPSRFSGSGSGTDFTLTI<br>NSVESEDIADYYCQQNNNWPTTFGQGTKLELKRT<br>V (SEQ ID NO: 12) |
| 22 | QVQLQQSGPGLVKPSETLSITCTVSGFSLTNYG<br>VHWVRQSPGKGLEWLGVIWSGGNTDYNTPFT<br>SRLTINKDNSKSQVFFKMNSLQSNDTAVYYCAR<br>ALTYYDYEFAYWGQGTLVTVSA (SEQ ID NO:<br>7) | DIVLTQSPDFQSVTPKEKVTITCRASQSIGTNIHWY<br>QQKPDQSPKLLIKYASESISGVPSRFSGSGSGTDFTL<br>TINSVESEDIADYYCQQNNNWPTTFGAGTKLELKR<br>TV (SEQ ID NO: 8) |
| 23 | QVQLQQSGPGLVKPSETLSITCTVSGFSLTNYG<br>VHWVRQSPGKGLEWLGVIWSGGNTDYNTPFT<br>SRLTINKDNSKSQVFFKMNSLQSNDTAVYYCAR<br>ALTYYDYEFAYWGQGTLVTVSA (SEQ ID NO:<br>7) | DIVLTQSPVFLSVTPGEKVTITCRASQSIGTNIHWY<br>QQKPDQSPKLLIKYASESISGVPSRFSGSGSGTDFTL<br>TINSVESEDIADYYCQQNNNWPTTFGAGTKLELKR<br>TV (SEQ ID NO: 9) |
| 24 | QVQLQQSGPGLVKPSETLSITCTVSGFSLTNYG<br>VHWVRQSPGKGLEWLGVIWSGGNTDYNTPFT<br>SRLTINKDNSKSQVFFKMNSLQSNDTAVYYCAR<br>ALTYYDYEFAYWGQGTLVTVSA (SEQ ID NO:<br>7) | DILLTQSPVILSVSPGERVTFSCRASQSIGTNIHWYQ<br>QKPDQSPKLLIKYASESISGVPSRFSGSGSGTDFTLTI<br>NSVESEDIADYYCQQNNNWPTTFGAGTKLELKRT<br>V (SEQ ID NO: 10) |

-continued

| # | sequence (heavy) | sequence (light) |
|---|---|---|
| 25 | QVQLQQSGPGLVKPSETLSITCTVSGFSLTNYG VHWVRQSPGKGLEWLGVIWSGGNTDYNTPFT SRLTINKDNSKSQVFFKMNSLQSNDTAVYYCAR ALTYYDYEFAYWGQGTLVTVSA (SEQ ID NO: 7) | DIVLTQSPVILSVSPGERVTFSCRASQSIGTNIHWYQ QKPDQSPKLLIKYASESISGVPSRFSGSGSGTDFTLTI NSVESEDIADYYCQQNNNWPTTFGQGTKLELKRT V (SEQ ID NO: 11) |
| 26 | QVQLQQSGPGLVKPSETLSITCTVSGFSLTNYG VHWVRQSPGKGLEWLGVIWSGGNTDYNTPFT SRLTINKDNSKSQVFFKMNSLQSNDTAVYYCAR ALTYYDYEFAYWGQGTLVTVSA (SEQ ID NO: 7) | EIVLTQSPVILSVSPGERVTFSCRASQSIGTNIHWYQ QKTDQSPRLLIKYASESISGIPSRFSGSGSGTDFTLTI NSVESEDIADYYCQQNNWPTTFGQGTKLELKRT V (SEQ ID NO: 12) |

Polynucleotides, Vectors, and Host Cells

Nucleic acids encoding humanized and thermostabilized antibodies of the invention are provided. In one embodiment, the nucleic acid molecule encodes a heavy and/or a light chain of a humanized and thermostabilized immunoglobulin. In a preferred embodiment, a single nucleic acid encodes a heavy chain of a humanized and thermostabilized immunoglobulin and another nucleic acid molecule encodes the light chain of a humanized and thermostabilized immunoglobulin.

In order to express the heavy and/or light chain of the humanized and thermostabilized antibodies of the invention, the polynucleotides encoding said heavy and/or light chains are inserted into expression vectors such that the genes are operatively linked to transcriptional and translational sequences. Expression vectors include plasmids, YACs, cosmids, retrovirus, EBV-derived episomes, and all the other vectors that the skilled man will know to be convenient for ensuring the expression of said heavy and/or light chains. The skilled man will realize that the polynucleotides encoding the heavy and the light chains can be cloned into different vectors or in the same vector. In a preferred embodiment, said polynucleotides are cloned in the same vector.

Polynucleotides of the invention and vectors comprising these molecules can be used for the transformation of a suitable mammalian host cell. Transformation can be by any known method for introducing polynucleotides into a cell host. Such methods are well known of the man skilled in the art and include dextran-mediated transformation, calcium phosphate precipitation, polybrene-mediated transfection, protoplast fusion, electroporation, encapsulation of the polynucleotide into liposomes, biolistic injection and direct microinjection of DNA into nuclei.

Antibody Fragments

The antibodies of the present invention include both the full length antibodies discussed above, as well as epitope-binding fragments thereof. As used herein, "antibody fragments" include any portion of an antibody that retains the ability to bind to the epitope recognized by the full length antibody, generally termed "epitope-binding fragments." Examples of antibody fragments include, but are not limited to, Fab, Fab' and F(ab')2, Fd, single-chain Fvs (scFv), single-chain antibodies, disulfide-linked Fvs (dsFv) and fragments comprising either a VL or VH region. Epitope-binding fragments, including single-chain antibodies, may comprise the variable region(s) alone or in combination with the entirety or a portion of the following: hinge region, CH1, CH2, and CH3 domains.

Such fragments may contain one or both Fab fragments or the F(ab')2 fragment. Preferably, the antibody fragments contain all six CDRs of the whole antibody, although fragments containing fewer than all of such regions, such as three, four or five CDRs, are also functional. Further, the fragments may be or may combine members of any one of the following immunoglobulin classes: IgG, IgM, IgA, IgD, or IgE, and the subclasses thereof.

Fab and F(ab')2 fragments may be produced by proteolytic cleavage, using enzymes such as papain (Fab fragments) or pepsin (F(ab')2 fragments).

The "single-chain FVs" ("scFvs") fragments are epitope-binding fragments that contain at least one fragment of an antibody heavy chain variable region ($V_H$) linked to at least one fragment of an antibody light chain variable region ($V_L$). The linker may be a short, flexible peptide selected to assure that the proper three-dimensional folding of the $V_L$ and $V_H$ regions occurs once they are linked so as to maintain the target molecule binding-specificity of the whole antibody from which the single-chain antibody fragment is derived. The carboxyl terminus of the $V_L$ or $V_H$ sequence may be covalently linked by a linker to the amino acid terminus of a complementary $V_L$ or $V_H$ sequence.

Single-chain antibody fragments of the present invention contain amino acid sequences having at least one of the variable or complementarity determining regions (CDRs) of the whole antibodies described in this specification, but lack some or all of the constant domains of those antibodies. These constant domains are not necessary for antigen binding, but constitute a major portion of the structure of whole antibodies. Single-chain antibody fragments may therefore overcome some of the problems associated with the use of antibodies containing a part or all of a constant domain. For example, single-chain antibody fragments tend to be free of undesired interactions between biological molecules and the heavy-chain constant region, or other unwanted biological activity. Additionally, single-chain antibody fragments are considerably smaller than whole antibodies and may therefore have greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely to provoke an immune response in a recipient than whole antibodies.

Single-chain antibody fragments may be generated by molecular cloning, antibody phage display library or similar techniques well known to the skilled artisan. These proteins may be produced, for example, in eukaryotic cells or prokaryotic cells, including bacteria. The epitope-binding fragments of the present invention can also be generated using various phage display methods known in the art. In phage display methods, functional antibody domains are displayed on the surface of phage particles which carry the polynucleotide sequences encoding them. In particular, such phage can be utilized to display epitope-binding domains expressed from a repertoire or combinatorial antibody library (e.g., human or murine). Phage expressing an epitope-binding domain that binds the antigen of interest can be selected or identified with antigen, e.g., using labeled antigen bound or captured to a solid surface or bead. Phage used in these methods are typically filamentous phage including fd and M13 binding domains expressed from phage with Fab, Fv or disulfide-stabilized Fv antibody domains recombinantly fused to either the phage gene III or gene VIII protein.

Examples of phage display methods that can be used to make the epitope-binding fragments of the present invention include those disclosed in Brinkman et al., 1995, J. Immunol. Methods, 182: 41-50; Ames et al., 1995, J. Immunol. Methods, 184:177-186; Kettleborough et al., 1994, Eur. J. Immunol., 24: 952-958; Persic et al., 1997, Gene, 187: 9-18; Burton et al., 1994, Advances in Immunology, 57: 191-280; WO/1992/001047; WO 90/02809; WO 91/10737; WO 92/01047; WO 92/118619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

After phage selection, the regions of the phage encoding the fragments can be isolated and used to generate the epitope-binding fragments through expression in a chosen host, including mammalian cells, insect cells, plant cells, yeast, and bacteria, using recombinant DNA technology, e.g., as described in detail below. For example, techniques to recombinantly produce Fab, Fab' and F(ab')2 fragments can also be employed using methods known in the art such as those disclosed in WO 92/22324; Mullinax et al., 1992, BioTechniques, 12(6): 864-869; Sawai et al., 1995, AJRI, 34: 26-34; and Better et al., 1988, Science, 240:1041-1043; said references incorporated by reference in their entireties. Examples of techniques which can be used to produce single-chain Fvs and antibodies include those described in U.S. Pat. Nos. 4,946,778 and 5,258,498; Huston et al., 1991, Methods in Enzymology, 203: 46-88; Shu et al., 1993, PNAS, 90: 7995-7999; Skerra et al., 1988, Science, 240: 1038-1040.

Cetuximab, also known as Erbitux® and IMC-C225 or CMAB009, is a chimeric human/mouse antibody that binds to epidermal growth factor receptor (EGFR). Examples disclosing cetuximab and its use are disclosed in WO 96/040210; WO 99/060023; WO 00/069459; WO 02/045653; WO 04/085474; WO 05/051355; WO 07/127936; WO 07/147001; WO 09/062083; WO 10/056893; and WO 10/080463, each of which is incorporated herein by reference in its entirety.

As used herein, "thermostabilized" or "thermostability" refers to the quality of a protein or antibody to resist chemical or physical change as a result of increasing temperature. For the purposes of this invention, alterations to the amino acid sequence of an antibody may be made to increase the thermostability of said antibody compared to the parent antibody. Thermostability may be determined by any known method in the field, including the measurement of the antibody melting temperature (TM). Improvements in thermostability include increases in the TM by greater than or equal to 0.1° C. to greater than or equal to 10.0° C.

Methods of Treatment

As used herein, "treatment" is an approach for obtaining beneficial or desired clinical results. For purposes of this invention, beneficial or desired clinical results include, but are not limited to, one or more of the following: reducing the proliferation of (or destroying) neoplastic or cancerous cells, inhibiting metastasis of neoplastic cells, shrinking or decreasing the size of a tumor, remission of cancer, decreasing symptoms resulting from cancer, increasing the quality of life of those suffering from cancer, decreasing the dose of other medications required to treat cancer, delaying the progression of cancer, curing a cancer, and/or prolong survival of patients having cancer.

As used herein, an "effective dosage" or "effective amount" of drug, compound, or pharmaceutical composition is an amount sufficient to effect any one or more beneficial or desired results. In more specific aspects, an effective amount prevents, alleviates or ameliorates symptoms of disease, and/or prolongs the survival of the subject being treated. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing one or more symptoms of a disease such as, for example, cancer including, for example without limitation, gastric cancer, sarcoma, lymphoma, Hodgkin's lymphoma, leukemia, head and neck cancer, squamous cell head and neck cancer, thymic cancer, epithelial cancer, salivary cancer, liver cancer, stomach cancer, thyroid cancer, lung cancer, ovarian cancer, breast cancer, prostate cancer, esophageal cancer, pancreatic cancer, glioma, leukemia, multiple myeloma, renal cell carcinoma, bladder cancer, cervical cancer, choriocarcinoma, colorectal cancer, oral cancer, skin cancer, and melanoma, decreasing the dose of other medications required to treat the disease, enhancing the effect of another medication, and/or delaying the progression of the cancer in patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to, farm animals (e.g., cows, pigs, horses, chickens, etc.), sport animals, pets, primates, horses, dogs, cats, mice and rats.

The invention will be further illustrated in the following non-limiting examples.

EXAMPLES

Example 1. Computational Design

CoDAH (Computationally-Driven Antibody Humanization) (Choi, Hua, Sentman, Ackerman and Bailey-Kellogg, 2015, incorporated herein by reference) is a structure-based protein design method that optimizes variants of a parental Fv by selecting sets of allowed mutations according to in silico evaluation of their effects on humanness and stability.

Example 2. Humanness Analysis

The humanness of an antibody is assessed in terms of its human string content score (Lazar G A, Desjarlais J R, Jacinto J, Karki S, Hammond P W. A molecular immunology approach to antibody humanization and functional optimization. Mol Immunol 2007; 44:1986-98) (FIG. 1, left). Consider a single l-length peptide p starting at position i in an antibody chain (light or heavy). The results presented here, as well as by Lazar et al (supra) use I=9, as this represents the typical length of the core peptide binding an MHC (Parham P, Ohta T. Population biology of antigen presentation by MHC class I molecules. Science 1996; 272:67-74 and Reche P A, Reinherz E L. Sequence variability analysis of human class I and class II MHC molecules: functional and structural correlates of amino acid polymorphisms. J Mol Biol 2003; 331:623-41). The position-specific humanness score contributed by that peptide is its maximum identity to a corresponding peptide (i.e., also starting at position I) in an aligned human germline g from a set G of considered germlines.

$$\psi_i(p) \,| = \max_{g \in G}\left(\sum_{j=1}^{l} I\{p[j] = g[i+j-1]\}\right) \quad (1)$$

The indicator function I{ } is 1 if the predicate is true, i.e., the amino acid in the target antibody is the same as the corresponding one in the germline, and 0 otherwise. So the maximum score contributed by a peptide is 9, if all 9 of its amino acids are identical to corresponding amino acids in some germline sequence.

The HSC score of an entire antibody chain v is then the average over all its constituent peptides, scaled to a percentage (0-100).

$$HSC = \frac{100}{l(n-l+1)} \cdot \sum_{i=1}^{n-l+1} \psi_i(\{v[i], v[i+1], \ldots, v[i+8]\}) \quad (2)$$

Example 3. Evaluation of Structural Energy

Antibody stability (FIG. 1, right) is assessed by rotamer-based structural energies, with position-specific single and pairwise terms based on the AMBER force field. (Pearlman D A, Case D A, Caldwell J W, Ross W S, Cheatham T E, DeBolt S, Ferguson D, Seibel G, Kollman P. AMBER, a package of computer programs for applying molecular mechanics, normal mode analysis, molecular dynamics and free energy calculations to simulate the structural and energetic properties of molecules. Comput Phys Commun 1995; 91:1-41). A rotamer library (Lovell S C, Word J M, Richardson J S, Richardson D C. The penultimate rotamer library. Proteins 2000; 40:389-408) specifies a discrete set of possible side-chain conformations for both the original protein and possible substitutions, and an energy matrix is constructed by the OSPREY protein redesign software package. (Chen C-Y, Georgiev I, Anderson A C, Donald B R. Computational structure-based redesign of enzyme activity. Proc Natl Acad Sci 2009; 106:3764-9 and Gainza P, Roberts K E, Donald B R. Protein design using continuous rotamers. PLoS Comput Biol 2012; 8:e1002335). OSPREY eliminates rotamers necessitating steric clashes, as well as those that are probably not part of optimal or sufficiently near-optimal designs. (Goldstein R F. Efficient rotamer elimination applied to protein side-chains and related spin glasses. Biophys J 1994; 66:1335-40). Only the Fv region is considered in the energy calculations.

Example 4. Identification of Substitutions

The CDRs are not allowed to mutate during humanization. To identify CDRs, antibody sequences are annotated by the Kabat numbering scheme using the AbNum program. (Abhinandan K, Martin A C. Analysis and improvements to Kabat and structurally correct numbering of antibody variable domains. Mol Immunol 2008; 45:3832-9). Light chain CDRs are defined as residues 24-34 (L1), 50-56 (L2) and 89-97 (L3), and heavy chain CDRs are composed of residues 31-35 (H1), 50-65 (H2) and 95-102 (H3).

At each position, any amino acid that appears in some human germline antibody sequence at the corresponding aligned position is considered as a possible substitution. It is also possible to filter the set based on those that are sufficiently frequent, appear in particular germlines, or based on other criteria as desired.

Example 5. Structure-Based Antibody Humanization Algorithm

The humanization algorithm identifies the Pareto optimal protein designs, (He L, Friedman A M, Bailey-Kellogg C. A divide-and-conquer approach to determine the Pareto frontier for optimization of protein engineering experiments. Proteins 2012; 80:790-806) i.e., those making the best trade-offs between the 2 competing objectives of HSC score and rotamer-based energy. The algorithm follows a "sweep" approach analogous to that previously developed for enzyme deimmunization. (Parker A S, Choi Y, Griswold K E, Bailey-Kellogg C. Structure-guided deimmunization of therapeutic proteins. J Comput Biol 2013; 20:152-65). Initially, the HSC score (Eq. 1, above) is calculated for the original target antibody sequence. The lowest-energy variant with a better HSC score than that of the original is then optimized, moving one step to the right on the curve in FIG. 1. The process is then repeated, finding the minimum-energy variant among those with better HSC scores than the first variant, and so forth along the curve. After a complete curve has been generated, the process can be repeated to produce a next-to-optimal curve, constraining the sequences to differ by at least one mutation from those already identified. Further increasingly suboptimal curves can likewise be generated.

In order to optimize the minimum-energy variant achieving at least a specified HSC score, the integer programming formulation of Parker et al. (supra) is adapted to use HSC. The integer program represents a variant as a set of rotamers, some from the original sequence and some as substitutions, encoded by a set of binary variables: $S_{i,r}$ indicates whether or not the variant uses rotamer r at position i. In order to incorporate pairwise energy terms, the integer program also includes pair variables: $p_{ir,jt}$ indicates whether or not the variant uses both rotamer r at i and t at j. Finally, in order to assess and thereby constraint HSC score, the "window" binary variable $W_{i,p}$ is defined to indicate whether or not amino acids spanning positions i to i+I−1 (I=9 in this case) correspond to linear peptide p (i.e., a sequence of 9 amino acids). Only peptides with HSC scores better than the original sequence are allowed.

The objective function for the integer program is to minimize the energy E, computed as:

$$E = \sum_{i,r} s_{i,r} E_i(r) + \sum_{i,r,j,t} p_{ir,jt} E(r,t) \quad (3)$$

where $E_i(r)$ is the energy of rotamer rat position i and $E_{ij}(r,t)$ the pairwise energy between rotamers r at i and t at j.

During the sweep, the next variant is constrained to improve the HSC score beyond the value H for the previous variant:

$$\sum_{i,p} w_{i,p} \cdot \psi_i(p) \geq H + 1 \quad (4)$$

The variables are further constrained as follows, in order to ensure that the pair and window variables are consistent with the singleton variables, and that only one rotamer is taken at each position:

$$(\forall\, i, r, j > i) \sum_t p_{ir,jt} = s_{i,r} \quad (5)$$

$$(\forall\, j, t, i < j) \sum_r p_{ir,js} = s_{j,t} \quad (6)$$

$$(\forall\, i) \sum_r s_{i,r} = 1 \quad (7)$$

$$(\forall\, i, r \forall\, h \in 1 \ldots l) \sum_{p:p[h]=a(r)} w_{i,p} = s_{i+h-1,r} \quad (8)$$

where p[h] is the amino acid type at position h in peptide p, and a(r) is that of rotamer r.

Additionally the mutation load m can be constrained, specifying the number of rotamers that are not of the corresponding original amino acid type:

$$m = \sum_{i,r:t[i]\neq a(r)} s_{i,r} \quad (9)$$

where t[i] is the amino acid at position i in the original target.

Example 6. Humanness Analysis and CoDAH Antibody Variant Generation

The Human String Content (HSC) score (Lazar, Desjarlais, Jacinto, Karki and Hammond, 2007) assesses humanness as the extent of identity of nonamer peptides within a variant to corresponding nonamers within human germline antibody sequences. The heavy (VH) and light chain (Vκ) variable regions of cetuximab were aligned to a total of 212 unique VH and 85 Vκ human germline antibody sequences extracted from publicly available databases including VBASE and IMGT (Poiron et al., 2010, Retter et al., 2005).

Structure-based rotameric energies assess the energetic impacts of mutations according to a molecular mechanics force field. CoDAH uses one- and two-body energy potentials defined by the AMBER force field (Pearlman et al., 1995, Qiu et al., 1997) as implemented by OSPREY (Chen et al., 2009, Gainza et al., 2012). The Fv portion from a crystal structure of cetuximab (PDB code: 1YY8) was used to parameterize these energies.

Figure 2A:
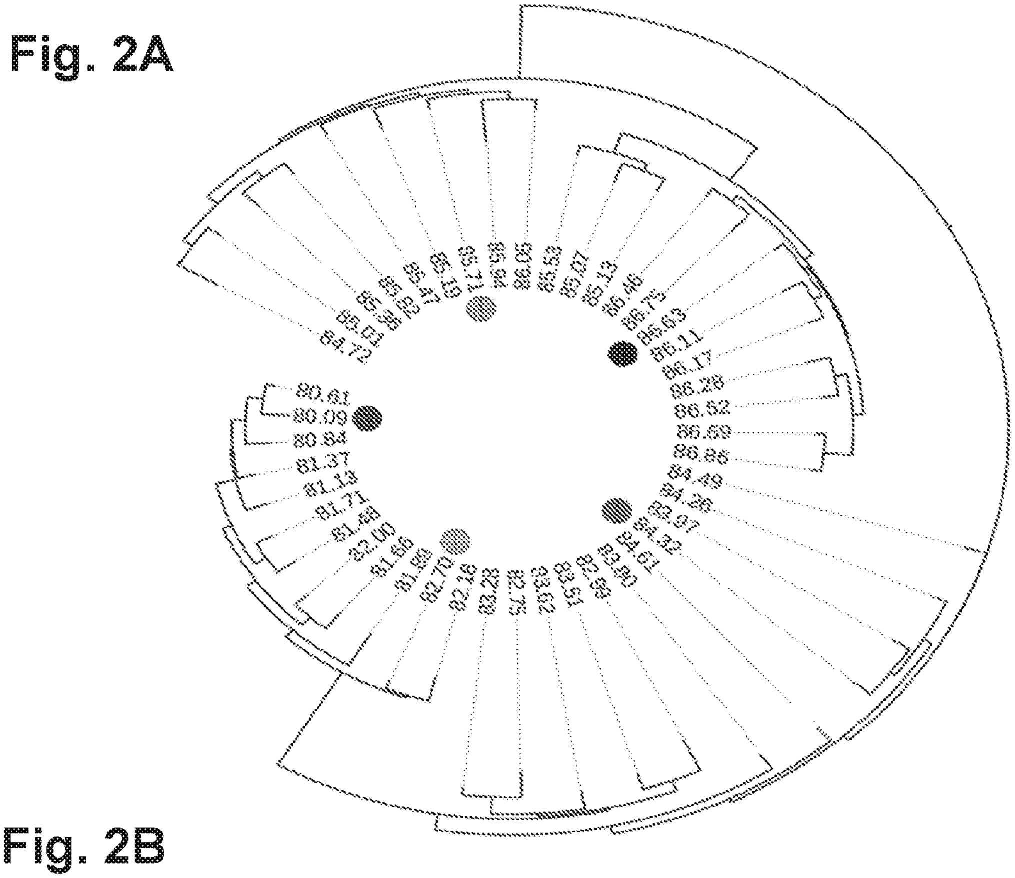
(FIG. 2A) CoDAH generated 43 Pareto optimal humanized variants of cetuximab. A phylogenetic tree of the designs is shown, where each design is annotated with its corresponding HSC score. Five different designs were selected so as to broadly sample sequence diversity and degree of humanness (circles).
Figure 2B:
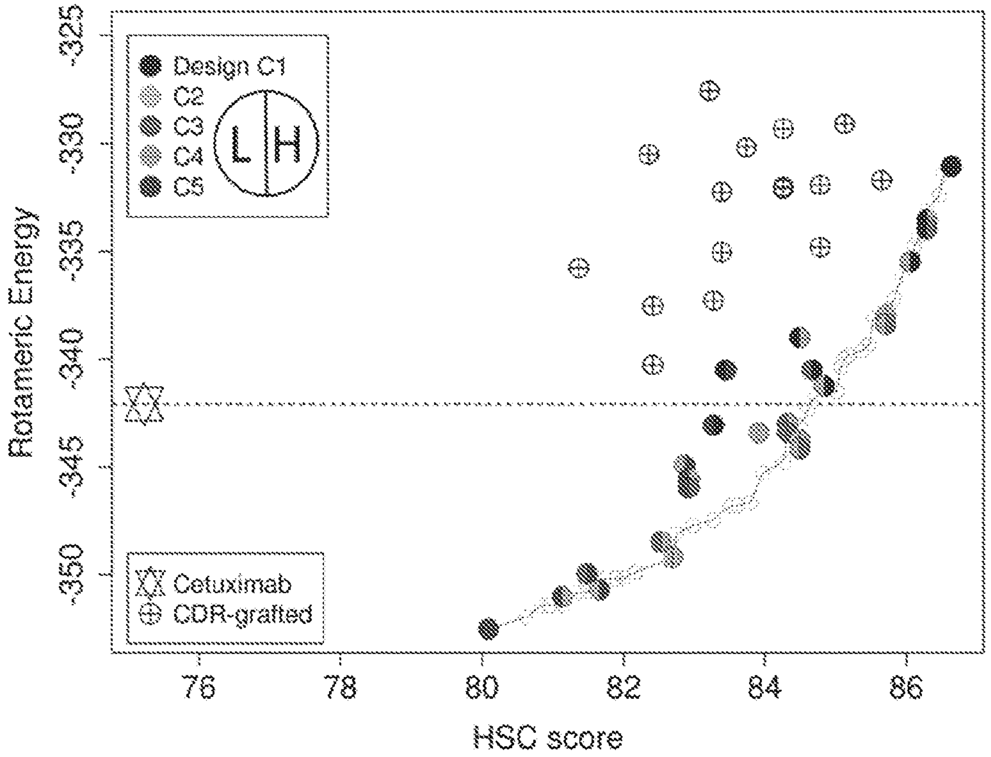
(FIG. 2B) For the selected CoDAH designs (solid colored circles), computed rotameric energies are plotted as a function of HSC score. CoDAH cross-pairs are also shown (2-tone circles, left: VL, right: VH), as are CDR-grafted designs (hatched black circles) and the cetuximab parental antibody (black star).

CoDAH generated a set of 43 Pareto optimal (He et al., 2012, Parker et al., 2013, Parker et al., 2010) integrated VH/Vκ cetuximab variants, those making the best trade-offs between the HSC score and rotameric energy (FIG. 2A). Five of these designs (FIG. 9, C1-05) were selected based on mutual sequence differences (FIG. 2B). See also Table 1 below for representative sequences. "N9" represents the number of nonamer peptides within a given antibody sequence that are an exact match to a human germline sequence. That value is given for combined heavy and light—"H9", for heavy chain only "N9_H", and for light chain only "N9_L".

TABLE 1

HSC scores and sequences of CoDAH-generated cetuximab variants.

| # | design_ Heavy Chain | design_ Light chain | energy | Human String Content (HSC) | HSC_ Heavy | HSC_ Light | N9 | N9_H | N9_L |
|---|---|---|---|---|---|---|---|---|---|
| 1 | Cetuximab | Cetuximab | -342.1 | 75.231 | 71.444 | 79.348 | 14 | 1 | 13 |
| 2 | C1 | C1 | -331.1 | 86.632 | 82.111 | 91.546 | 81 | 27 | 54 |
| 3 | C1 | C2 | -335.5 | 86.053 | 82.111 | 90.338 | 72 | 27 | 45 |
| 4 | C1 | C3 | -340.5 | 84.664 | 82.111 | 87.440 | 60 | 27 | 33 |
| 5 | C1 | C4 | -341.2 | 84.838 | 82.111 | 87.802 | 60 | 27 | 33 |
| 6 | C1 | C5 | -343.1 | 83.275 | 82.111 | 84.541 | 44 | 27 | 17 |
| 7 | C2 | C1 | -333.5 | 86.285 | 81.444 | 91.546 | 77 | 23 | 54 |
| 8 | C2 | C2 | -338.0 | 85.706 | 81.444 | 90.338 | 68 | 23 | 45 |
| 9 | C2 | C3 | -343.0 | 84.317 | 81.444 | 87.440 | 56 | 23 | 33 |
| 10 | C2 | C4 | -343.7 | 84.491 | 81.444 | 87.802 | 56 | 23 | 33 |

TABLE 1-continued

HSC scores and sequences of CoDAH-generated cetuximab variants.

| | | | | | | | | | |
|---|---|---|---|---|---|---|---|---|---|
| 11 | C2 | C5 | -345.6 | 82.928 | 81.444 | 84.541 | 40 | 23 | 17 |
| 12 | C3 | C1 | -334.0 | 86.285 | 81.444 | 91.546 | 77 | 23 | 54 |
| 13 | C3 | C2 | -338.4 | 85.706 | 81.444 | 90.338 | 68 | 23 | 45 |
| 14 | C3 | C3 | -343.4 | 84.317 | 81.444 | 87.440 | 56 | 23 | 33 |
| 15 | C3 | C4 | -344.1 | 84.491 | 81.444 | 87.802 | 56 | 23 | 33 |
| 16 | C3 | C5 | -346.0 | 82.928 | 81.444 | 84.541 | 40 | 23 | 17 |
| 17 | C4 | C1 | -339.0 | 84.491 | 78 | 91.546 | 75 | 21 | 54 |
| 18 | C4 | C2 | -343.4 | 83.912 | 78 | 90.338 | 66 | 21 | 45 |
| 19 | C4 | C3 | -348.5 | 82.523 | 78 | 87.440 | 54 | 21 | 33 |
| 20 | C4 | C4 | -349.2 | 82.697 | 78 | 87.802 | 54 | 21 | 33 |
| 21 | C4 | C5 | -351.0 | 81.134 | 78 | 84.541 | 38 | 21 | 17 |
| 22 | C5 | C1 | -340.5 | 83.449 | 76 | 91.546 | 67 | 13 | 54 |
| 23 | C5 | C2 | -344.9 | 82.870 | 76 | 90.338 | 58 | 13 | 45 |
| 24 | C5 | C3 | -350.0 | 81.481 | 76 | 87.440 | 46 | 13 | 33 |
| 25 | C5 | C4 | -350.7 | 81.655 | 76 | 87.802 | 46 | 13 | 33 |
| 26 | C5 | C5 | -352.5 | 80.093 | 76 | 84.541 | 30 | 13 | 17 |

| # | sequence (heavy) | sequence (light) |
|---|---|---|
| 1 | QVQLKQSGPGLVQPSQSLSITCTVSGFSLTNYG<br>VHWVRQSPGKGLEWLGVIWSGGNTDYNTPFT<br>SRLSINKDNSKSQVFFKMNSLQSNDTAIYYCAR<br>ALTYYDYEFAYWGQGTLVTVSA (SEQ ID NO:<br>1) | DILLTQSPVILSVSPGERVSFSCRASQSIGTNIHWYQ<br>QRTNGSPRLLIKYASESISGIPSRFSGSGSGTDFTLSI<br>NSVESEDIADYYCQQNNNWPTTFGAGTKLELKRT<br>V (SEQ ID NO: 2) |
| 2 | QVQLQQSGPGLVKPSQTLSLTCTVSGFSLTNYG<br>VHWVRQSPGKGLEWLGVIWSGGNTDYNTPFT<br>SRLTISKDTSKNQVSLKLSSVTSNDTAVYYCARA<br>LTYYDYEFAYWGQGTLVTVSA (SEQ ID NO: 3) | DIVLTQSPDFQSVTPKEKVTITCRASQSIGTNIHWY<br>QQKPDQSPKLLIKYASESISGVPSRFSGSGSGTDFTL<br>TINSVESEDIADYYCQQNNNWPTTFGAGTKLELKR<br>TV (SEQ ID NO: 8) |
| 3 | QVQLQQSGPGLVKPSQTLSLTCTVSGFSLTNYG<br>VHWVRQSPGKGLEWLGVIWSGGNTDYNTPFT<br>SRLTISKDTSKNQVSLKLSSVTSNDTAVYYCARA<br>LTYYDYEFAYWGQGTLVTVSA (SEQ ID NO: 3) | DIVLTQSPVFLSVTPGEKVTITCRASQSIGTNIHWY<br>QQKPDQSPKLLIKYASESISGVPSRFSGSGSGTDFTL<br>TINSVESEDIADYYCQQNNNWPTTFGAGTKLELKR<br>TV (SEQ ID NO: 9) |
| 4 | QVQLQQSGPGLVKPSQTLSLTCTVSGFSLTNYG<br>VHWVRQSPGKGLEWLGVIWSGGNTDYNTPFT<br>SRLTISKDTSKNQVSLKLSSVTSNDTAVYYCARA<br>LTYYDYEFAYWGQGTLVTVSA (SEQ ID NO: 3) | DILLTQSPVILSVSPGERVTFSCRASQSIGTNIHWYQ<br>QKPDQSPKLLIKYASESISGVPSRFSGSGSGTDFTLTI<br>NSVESEDIADYYCQQNNNWPTTFGAGTKLELKRT<br>V (SEQ ID NO: 10) |
| 5 | QVQLQQSGPGLVKPSQTLSLTCTVSGFSLTNYG<br>VHWVRQSPGKGLEWLGVIWSGGNTDYNTPFT<br>SRLTISKDTSKNQVSLKLSSVTSNDTAVYYCARA<br>LTYYDYEFAYWGQGTLVTVSA (SEQ ID NO: 3) | DIVLTQSPVILSVSPGERVTFSCRASQSIGTNIHWYQ<br>QKPDQSPKLLIKYASESISGVPSRFSGSGSGTDFTLTI<br>NSVESEDIADYYCQQNNNWPTTFGQGTKLELKRT<br>V (SEQ ID NO: 11) |
| 6 | QVQLQQSGPGLVKPSQTLSLTCTVSGFSLTNYG<br>VHWVRQSPGKGLEWLGVIWSGGNTDYNTPFT<br>SRLTISKDTSKNQVSLKLSSVTSNDTAVYYCARA<br>LTYYDYEFAYWGQGTLVTVSA (SEQ ID NO: 3) | EIVLTQSPVILSVSPGERVTFSCRASQSIGTNIHWYQ<br>QKTDQSPRLLIKYASESISGIPSRFSGSGSGTDFTLTI<br>NSVESEDIADYYCQQNNNWPTTFGQGTKLELKRT<br>V (SEQ ID NO: 12) |
| 7 | QVQLQQSGPGLVKPSQTLSLTCTVSGFSLTNYG<br>VHWVRQSPGKGLEWLGVIWSGGNTDYNTPFT<br>SRLTISVDTSKNQVSLKLSSVTSNDTAVYYCARA<br>LTYYDYEFAYWGQGTLVTVSA (SEQ ID NO: 4) | DIVLTQSPDFQSVTPKEKVTITCRASQSIGTNIHWY<br>QQKPDQSPKLLIKYASESISGVPSRFSGSGSGTDFTL<br>TINSVESEDIADYYCQQNNNWPTTFGAGTKLELKR<br>TV (SEQ ID NO: 8) |
| 8 | QVQLQQSGPGLVKPSQTLSLTCTVSGFSLTNYG<br>VHWVRQSPGKGLEWLGVIWSGGNTDYNTPFT<br>SRLTISVDTSKNQVSLKLSSVTSNDTAVYYCARA<br>LTYYDYEFAYWGQGTLVTVSA (SEQ ID NO: 4) | DIVLTQSPVFLSVTPGEKVTITCRASQSIGTNIHWY<br>QQKPDQSPKLLIKYASESISGVPSRFSGSGSGTDFTL<br>TINSVESEDIADYYCQQNNNWPTTFGAGTKLELKR<br>TV (SEQ ID NO: 9) |

TABLE 1-continued

| HSC scores and sequences of CoDAH-generated cetuximab variants. | | |
|---|---|---|
| 9 | QVQLQQSGPGLVKPSQTLSLTCTVSGFSLTNYGVHWVRQSPGKGLEWLGVIWSGGNTDYNTPFTSRLTISVDTSKNQVSLKLSSVTSNDTAVYYCARALTYYDYEFAYWGQGTLVTVSA (SEQ ID NO: 4) | DILLTQSPVILSVSPGERVTFSCRASQSIGTNIHWYQQKPDQSPKLLIKYASESISGVPSRFSGSGSGTDFTLTINSVESEDIADYYCQQNNNWPTTFGAGTKLELKRTV (SEQ ID NO: 10) |
| 10 | QVQLQQSGPGLVKPSQTLSLTCTVSGFSLTNYGVHWVRQSPGKGLEWLGVIWSGGNTDYNTPFTSRLTISVDTSKNQVSLKLSSVTSNDTAVYYCARALTYYDYEFAYWGQGTLVTVSA (SEQ ID NO: 4) | DIVLTQSPVILSVSPGERVTFSCRASQSIGTNIHWYQQKPDQSPKLLIKYASESISGVPSRFSGSGSGTDFTLTINSVESEDIADYYCQQNNNWPTTFGQGTKLELKRTV (SEQ ID NO: 11) |
| 11 | QVQLQQSGPGLVKPSQTLSLTCTVSGFSLTNYGVHWVRQSPGKGLEWLGVIWSGGNTDYNTPFTSRLTISVDTSKNQVSLKLSSVTSNDTAVYYCARALTYYDYEFAYWGQGTLVTVSA (SEQ ID NO: 4) | EIVLTQSPVILSVSPGERVTFSCRASQSIGTNIHWYQQKTDQSPRLLIKYASESISGIPSRFSGSGSGTDFTLTINSVESEDIADYYCQQNNNWPTTFGQGTKLELKRTV (SEQ ID NO: 12) |
| 12 | QVQLQQSGPGLVKPSETLSLTCTVSGFSLTNYGVHWVRQSPGKGLEWLGVIWSGGNTDYNTPFTSRLTISVDTSKNQVSLKLSSVTSNDTAVYYCARALTYYDYEFAYWGQGTLVTVSA (SEQ ID NO: 5) | DIVLTQSPDFQSVTPKEKVTITCRASQSIGTNIHWYQQKPDQSPKLLIKYASESISGVPSRFSGSGSGTDFTLTINSVESEDIADYYCQQNNNWPTTFGAGTKLELKRTV (SEQ ID NO: 8) |
| 13 | QVQLQQSGPGLVKPSETLSLTCTVSGFSLTNYGVHWVRQSPGKGLEWLGVIWSGGNTDYNTPFTSRLTISVDTSKNQVSLKLSSVTSNDTAVYYCARALTYYDYEFAYWGQGTLVTVSA (SEQ ID NO: 5) | DIVLTQSPVFLSVTPGEKVTITCRASQSIGTNIHWYQQKPDQSPKLLIKYASESISGVPSRFSGSGSGTDFTLTINSVESEDIADYYCQQNNNWPTTFGAGTKLELKRTV (SEQ ID NO: 9) |
| 14 | QVQLQQSGPGLVKPSETLSLTCTVSGFSLTNYGVHWVRQSPGKGLEWLGVIWSGGNTDYNTPFTSRLTISVDTSKNQVSLKLSSVTSNDTAVYYCARALTYYDYEFAYWGQGTLVTVSA (SEQ ID NO: 5) | DILLTQSPVILSVSPGERVTFSCRASQSIGTNIHWYQQKPDQSPKLLIKYASESISGVPSRFSGSGSGTDFTLTINSVESEDIADYYCQQNNNWPTTFGAGTKLELKRTV (SEQ ID NO: 10) |
| 15 | QVQLQQSGPGLVKPSETLSLTCTVSGFSLTNYGVHWVRQSPGKGLEWLGVIWSGGNTDYNTPFTSRLTISVDTSKNQVSLKLSSVTSNDTAVYYCARALTYYDYEFAYWGQGTLVTVSA (SEQ ID NO: 5) | DIVLTQSPVILSVSPGERVTFSCRASQSIGTNIHWYQQKPDQSPKLLIKYASESISGVPSRFSGSGSGTDFTLTINSVESEDIADYYCQQNNNWPTTFGQGTKLELKRTV (SEQ ID NO: 11) |
| 16 | QVQLQQSGPGLVKPSETLSLTCTVSGFSLTNYGVHWVRQSPGKGLEWLGVIWSGGNTDYNTPFTSRLTISVDTSKNQVSLKLSSVTSNDTAVYYCARALTYYDYEFAYWGQGTLVTVSA (SEQ ID NO: 5) | EIVLTQSPVILSVSPGERVTFSCRASQSIGTNIHWYQQKTDQSPRLLIKYASESISGIPSRFSGSGSGTDFTLTINSVESEDIADYYCQQNNNWPTTFGQGTKLELKRTV (SEQ ID NO: 12) |
| 17 | QVQLQQSGPGLVKPSQTLSLTCTVSGFSLTNYGVHWVRQSPGKGLEWLGVIWSGGNTDYNTPFTSRLTISKDNSKSQVFFKMNSLQSNDTAVYYCARALTYYDYEFAYWGQGTLVTVSA (SEQ ID NO: 6) | DIVLTQSPDFQSVTPKEKVTITCRASQSIGTNIHWYQQKPDQSPKLLIKYASESISGVPSRFSGSGSGTDFTLTINSVESEDIADYYCQQNNNWPTTFGAGTKLELKRTV (SEQ ID NO: 8) |
| 18 | QVQLQQSGPGLVKPSQTLSLTCTVSGFSLTNYGVHWVRQSPGKGLEWLGVIWSGGNTDYNTPFTSRLTISKDNSKSQVFFKMNSLQSNDTAVYYCARALTYYDYEFAYWGQGTLVTVSA (SEQ ID NO: 6) | DIVLTQSPVFLSVTPGEKVTITCRASQSIGTNIHWYQQKPDQSPKLLIKYASESISGVPSRFSGSGSGTDFTLTINSVESEDIADYYCQQNNNWPTTFGAGTKLELKRTV SEQ ID NO: 9) |
| 19 | QVQLQQSGPGLVKPSQTLSLTCTVSGFSLTNYGVHWVRQSPGKGLEWLGVIWSGGNTDYNTPFTSRLTISKDNSKSQVFFKMNSLQSNDTAVYYCARALTYYDYEFAYWGQGTLVTVSA (SEQ ID NO: 6) | DILLTQSPVILSVSPGERVTFSCRASQSIGTNIHWYQQKPDQSPKLLIKYASESISGVPSRFSGSGSGTDFTLTINSVESEDIADYYCQQNNNWPTTFGAGTKLELKRTV (SEQ ID NO: 10) |
| 20 | QVQLQQSGPGLVKPSQTLSLTCTVSGFSLTNYGVHWVRQSPGKGLEWLGVIWSGGNTDYNTPFTSRLTISKDNSKSQVFFKMNSLQSNDTAVYYCARALTYYDYEFAYWGQGTLVTVSA (SEQ ID NO: 6) | DIVLTQSPVILSVSPGERVTFSCRASQSIGTNIHWYQQKPDQSPKLLIKYASESISGVPSRFSGSGSGTDFTLTINSVESEDIADYYCQQNNNWPTTFGQGTKLELKRTV (SEQ ID NO: 11) |
| 21 | QVQLQQSGPGLVKPSQTLSLTCTVSGFSLTNYGVHWVRQSPGKGLEWLGVIWSGGNTDYNTPFTSRLTISKDNSKSQVFFKMNSLQSNDTAVYYCARALTYYDYEFAYWGQGTLVTVSA (SEQ ID NO: 6) | EIVLTQSPVILSVSPGERVTFSCRASQSIGTNIHWYQQKTDQSPRLLIKYASESISGIPSRFSGSGSGTDFTLTINSVESEDIADYYCQQNNNWPTTFGQGTKLELKRTV (SEQ ID NO: 12) |
| 22 | QVQLQQSGPGLVKPSETLSITCTVSGFSLTNYGVHWVRQSPGKGLEWLGVIWSGGNTDYNTPFTSRLTINKDNSKSQVFFKMNSLQSNDTAVYYCARALTYYDYEFAYWGQGTLVTVSA (SEQ ID NO: 7) | DIVLTQSPDFQSVTPKEKVTITCRASQSIGTNIHWYQQKPDQSPKLLIKYASESISGVPSRFSGSGSGTDFTLTINSVESEDIADYYCQQNNNWPTTFGAGTKLELKRTV (SEQ ID NO: 8) |

TABLE 1-continued

| HSC scores and sequences of CoDAH-generated cetuximab variants. | | |
|---|---|---|
| 23 | QVQLQQSGPGLVKPSETLSITCTVSGFSLTNYG VHWVRQSPGKGLEWLGVIWSGGNTDYNTPFT SRLTINKDNSKSQVFFKMNSLQSNDTAVYYCAR ALTYYDYEFAYWGQGTLVTVSA (SEQ ID NO: 7) | DIVLTQSPVFLSVTPGEKVTITCRASQSIGTNIHWY QQKPDQSPKLLIKYASESISGVPSRFSGSGSGTDFTL TINSVESEDIADYYCQQNNNWPTTFGAGTKLELKR TV (SEQ ID NO: 9) |
| 24 | QVQLQQSGPGLVKPSETLSITCTVSGFSLTNYG VHWVRQSPGKGLEWLGVIWSGGNTDYNTPFT SRLTINKDNSKSQVFFKMNSLQSNDTAVYYCAR ALTYYDYEFAYWGQGTLVTVSA (SEQ ID NO: 7) | DILLTQSPVILSVSPGERVTFSCRASQSIGTNIHWYQ QKPDQSPKLLIKYASESISGVPSRFSGSGSGTDFTLTI NSVESEDIADYYCQQNNNWPTTFGAGTKLELKRT V (SEQ ID NO: 10) |
| 25 | QVQLQQSGPGLVKPSETLSITCTVSGFSLTNYG VHWVRQSPGKGLEWLGVIWSGGNTDYNTPFT SRLTINKDNSKSQVFFKMNSLQSNDTAVYYCAR ALTYYDYEFAYWGQGTLVTVSA (SEQ ID NO: 7) | DIVLTQSPVILSVSPGERVTFSCRASQSIGTNIHWYQ QKPDQSPKLLIKYASESISGVPSRFSGSGSGTDFTLTI NSVESEDIADYYCQQNNNWPTTFGQGTKLELKRT V (SEQ ID NO: 11) |
| 26 | QVQLQQSGPGLVKPSETLSITCTVSGFSLTNYG VHWVRQSPGKGLEWLGVIWSGGNTDYNTPFT SRLTINKDNSKSQVFFKMNSLQSNDTAVYYCAR ALTYYDYEFAYWGQGTLVTVSA (SEQ ID NO: 7) | EIVLTQSPVILSVSPGERVTFSCRASQSIGTNIHWYQ QKTDQSPRLLIKYASESISGIPSRFSGSGSGTDFTLTI NSVESEDIADYYCQQNNNWPTTFGQGTKLELKRT V (SEQ ID NO: 12) |

Example 7. Cetuximab CDR Sequences

As a comparator, a panel of humanized variants was also constructed using a conventional approach to CDR grafting. The CDRs of cetuximab (defined by the Kabat numbering scheme, see Table 2 below) were grafted onto the most similar human germline antibodies from the databases. Select murine framework residues were retained based on knowledge of packing in the immunoglobulin fold (Chothia et al., 1998), the surface accessibility (Pedersen et al., 1994), the interface regions of VH/VL (Chothia et al., 1985), the Vernier zone (Foote and Winter, 1992) and other known risk factors (Studnicka et al., 1994). In total, four CDR-grafted designs were selected for each chain (FIG. 9, G1-G4).

TABLE 2

| Cetuximab CDR sequences | |
|---|---|
| CDR | Sequence |
| HCDR1 | NYGVH (SEQ ID NO: 13) |
| HCDR2 | VIWSGGNTDYNTPFTS (SEQ ID NO: 14) |
| HCDR3 | ALTYYDYEFAY (SEQ ID NO: 15) |
| LCDR1 | RASQSIGTNIH (SEQ ID NO: 16) |
| LCDR2 | YASESIS (SEQ ID NO: 17) |
| LCDR3 | QQNNNWPTT (SEQ ID NO: 18) |

Gene Construction, Protein Expression, and Antibody Purification

Following in-house design of both CoDAH and CDR grafted antibodies, a commercial service provider was contracted to synthesize, clone, express via transient transfection in HEK cells, and purify all constructs (MIGS LLC, Lebanon, N.H., USA). In addition to the five CoDAH designs with jointly optimized VH/Vκ pairs (FIG. 9, C1-05), the cross VH/Vκ pairs were also constructed, creating 20 cross pairs for a total of 25 CoDAH antibodies (also plotted in FIG. 2A). CDR grafting had no preferred pairs, so the four CDR-grafted VH were likewise paired with each of the four CDR-grafted Vκ (FIG. 9, G1-G5), for a total of 16 pairs.

Figure 3A:
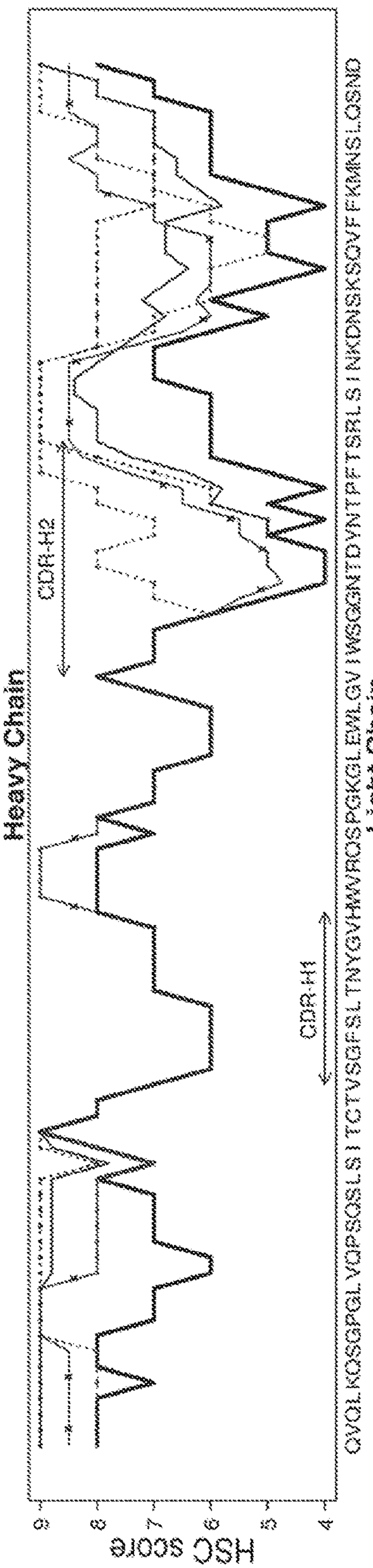
FIG. 3A displays SEQ ID NO: 32 and FIG. 3B displays SEQ ID NO: 33.
Figure 3B:
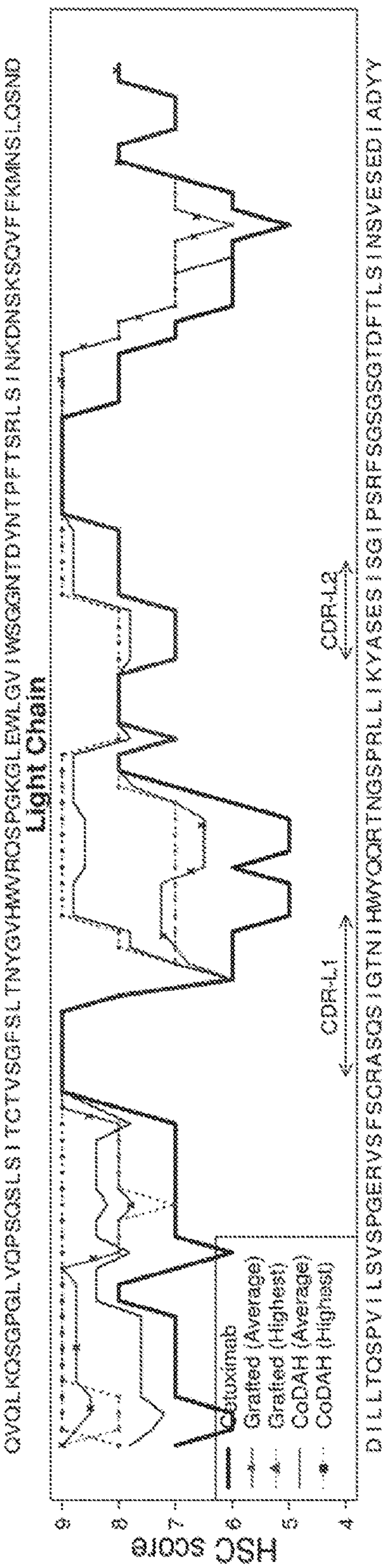
FIG. 3. Positional HSC of CoDAH (light solid and circle line) and grafted (x and triangle line) designs in (FIG. 3A) heavy and (FIG. 3B) light chains. Note that CDR 3s are not labeled due to lack of germline sequences.
(FIG. 3C) On average, both design strategies yield similar levels of overall HSC scores.
(FIG. 3D) Compared to CDR-grafting, CoDAH designs generally contain more exact nonamer matches against human germline antibody sequences.
Figure 3C:
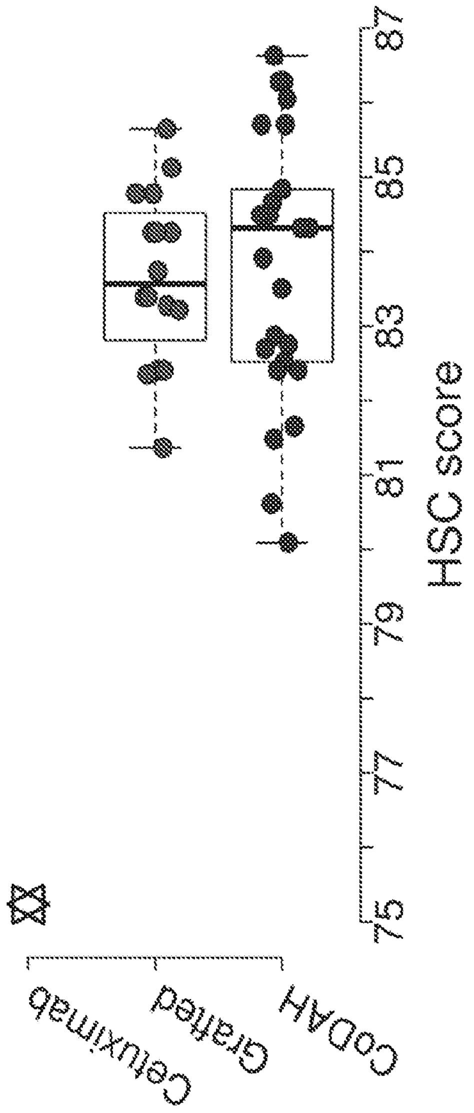
Figure 3D:
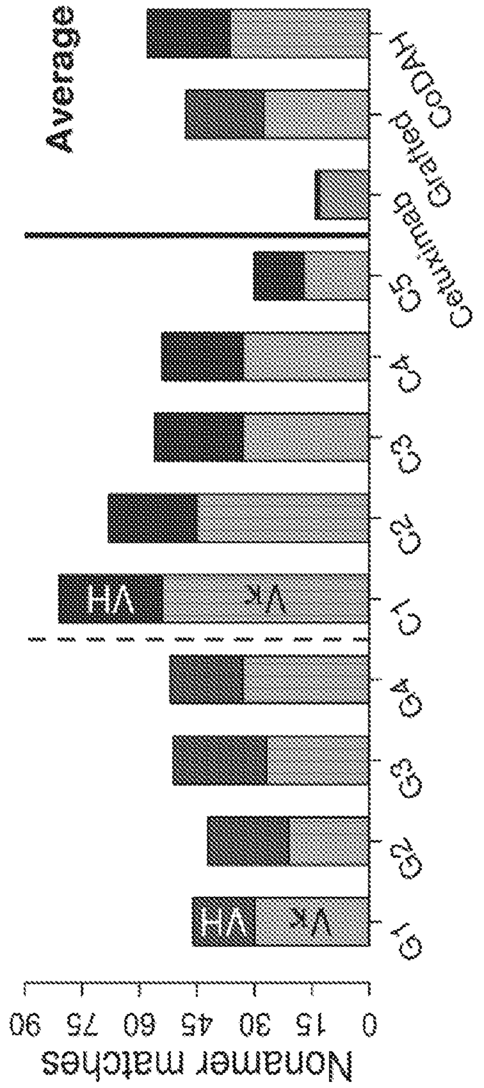
Figure 4:
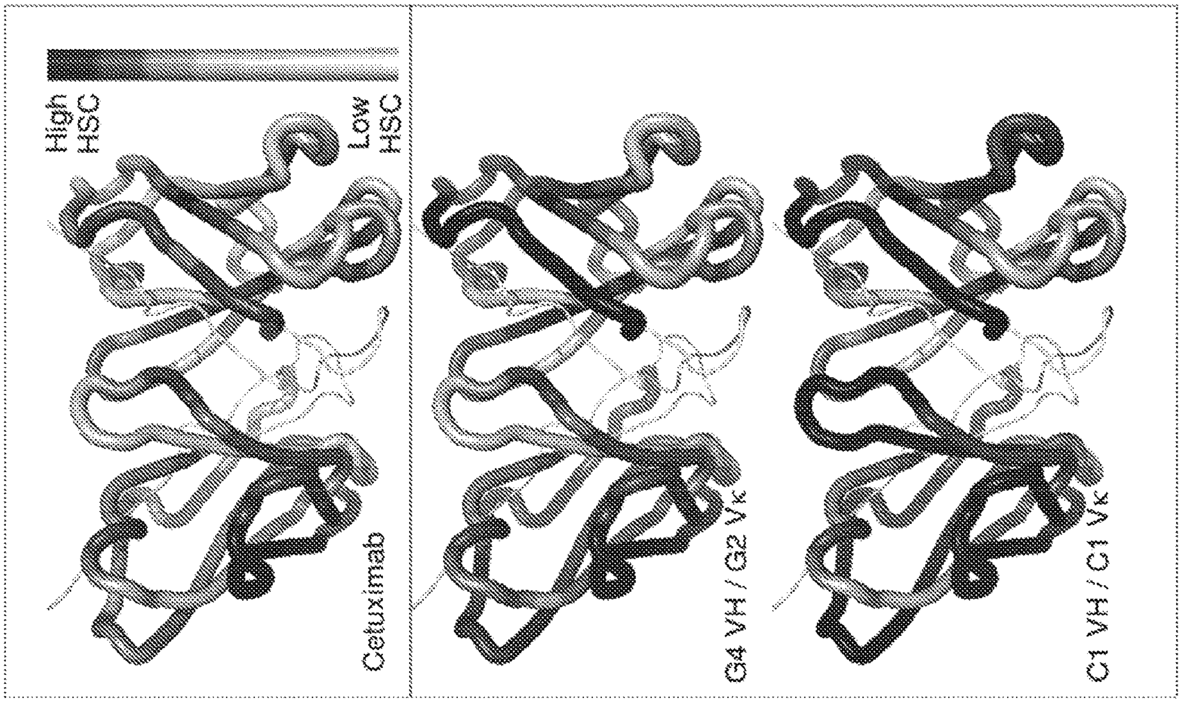
FIG. 4. Visualization of HSC scores for the CoDAH and grafted designs with the best HSC scores, where darker color indicates higher HSC at the corresponding position. The CoDAH design (C1 Vκ and C1 VH) tends to have more nonamer matches than the grafted design (G2 Vκ and G4 VH), e.g. compare shading at center and far right of structures.

On average, CDR-grafted and CoDAH humanized antibody designs possessed similar levels of humanness. Their average HSC scores (CoDAH: 83.8 and grafted: 83.7) were similar across all the designs (FIG. 2B and FIG. 3C), and superior to cetuximab (75.2). However, CoDAH designs tended to have more exact matches against human germline nonamers (CoDAH: 57.8 [VH 21.4+Vκ 36.4] and grafted: 47.8 [20+27.8], compared to cetuximab: 14 [1+13]; FIG. 3D and FIG. 4). Furthermore, the most optimized CoDAH designs (C2 or C3 VH, and C1 Vκ) were highly similar to human germline chains (FIG. 9), with only 13 positional differences (7 for VH+6 for Vκ, excluding CDR loops) from the closest germline antibody chains, whereas there were 16 positional differences (7+9) between the most similar grafted design (G3 VH and G4 Vκ) and its corresponding germline sequence.

To facilitate comparison with traditional CDR grafting, the allowed mutations were restricted to those from a small set of the most-similar germline sequences: three for VH (IGHV4-4, 34 and 59) and two for Vκ (IGKV6D-21 and 41). Mutations were not allowed within the complementarity determining regions (CDRs), as defined by the Kabat numbering scheme using the AbNum program (Abhinandan and Martin, 2008). No further restrictions were imposed on allowed mutations.

Representative human germline sequences for IGHV4-4, IGHV4-34, IGHV4-59, IGKV6D-21, and IGKV6D-41 are shown below in Table 3.

TABLE 3

| Select human germline sequences | |
|---|---|
| Gene | Sequence |
| IGHV4-4 | QVQLQESGPGLVKPPGTLSLTCAVSGGSISSSNWWSWVRQ PPGKGLEWIGEIYHSGSTNYNPSLKSRVTISVDKSKNQFS LKLSSVTAADTAVYCCAR (SEQ ID NO: 19) |
| IGHV4-34 | QVQLQQWGAGLLKPSETLSLTCAVYGGSFSGYYWSWIRQP PGKGLEWIGEINHSGSTNYNPSLKSRVTISVDTSKNQFSL KLSSVTAADTAVYYCAR (SEQ ID NO: 20) |

TABLE 3-continued

| Select human germline sequences | |
|---|---|
| Gene | Sequence |
| IGHV4-59 | QVQLQESGPGLVKPSETLSLTCTVSGGSISSYYWSWIRQP PGKGLEWIGYIYYSGSTNYNPSLKSRVTISVDTSKNQFSL KLSSVTAADTAVYYCAR (SEQ ID NO: 21) |
| IGKV6D-21 | EIVLTQSPDFQSVTPKEKVTITCRASQSIGSSLHWYQQKP DQSPKLLIKYASQSFSGVPSRFSGSGSGTDFTLTINSLEA EDAATYYCHQSSSLP (SEQ ID NO: 22) |
| IGKV6D-41 | DVVMTQSPAFLSVTPGEKVTITCQASEGIGNYLYWYQQKP DQAPKLLIKYASQSISGVPSRFSGSGSGTDFTFTISSLEA EDAATYYCQQGNKHP (SEQ ID NO: 23) |

Example 3. Thermostability and Binding Affinity

The relative stability of all constructs, formatted as Fab fragments, was analyzed by differential scanning fluorimetry (DSF) (Niesen, Berglund and Vedadi, 2007) using an ABI 7500 Fast Real-Time PCR System from Applied Biosystems. Proteins and SYPRO Orange were diluted in PBS. Final protein concentrations were 100 μg/ml and final dye concentrations were 5×. The PCR gradient was run from 25-98° C. with a 1 min equilibration at each degree centigrade. Fluorescence was quantified using the preset TAMRA parameters. To eliminate confounding signals from Fc denaturation, thermostability was determined using recombinant Fab fragments. Since some of the Fabs displayed multi-transition melting curves, fractional melting temperatures were computed by analyzing local transitions, ignoring those that plateaued below arbitrarily chosen thresholds (i.e., indicating relatively minor unfolding). For example, TM20* was computed from the minimum intensity to the first local plateau exceeding 20% of the total fluorescence signal (ignoring both transitions below 20% and any above the first local transition, where observed). Values for TM10* and TM50* were likewise determined, while TM100* indicates the midpoint between the minimum and maximum intensities.

Figure 5:
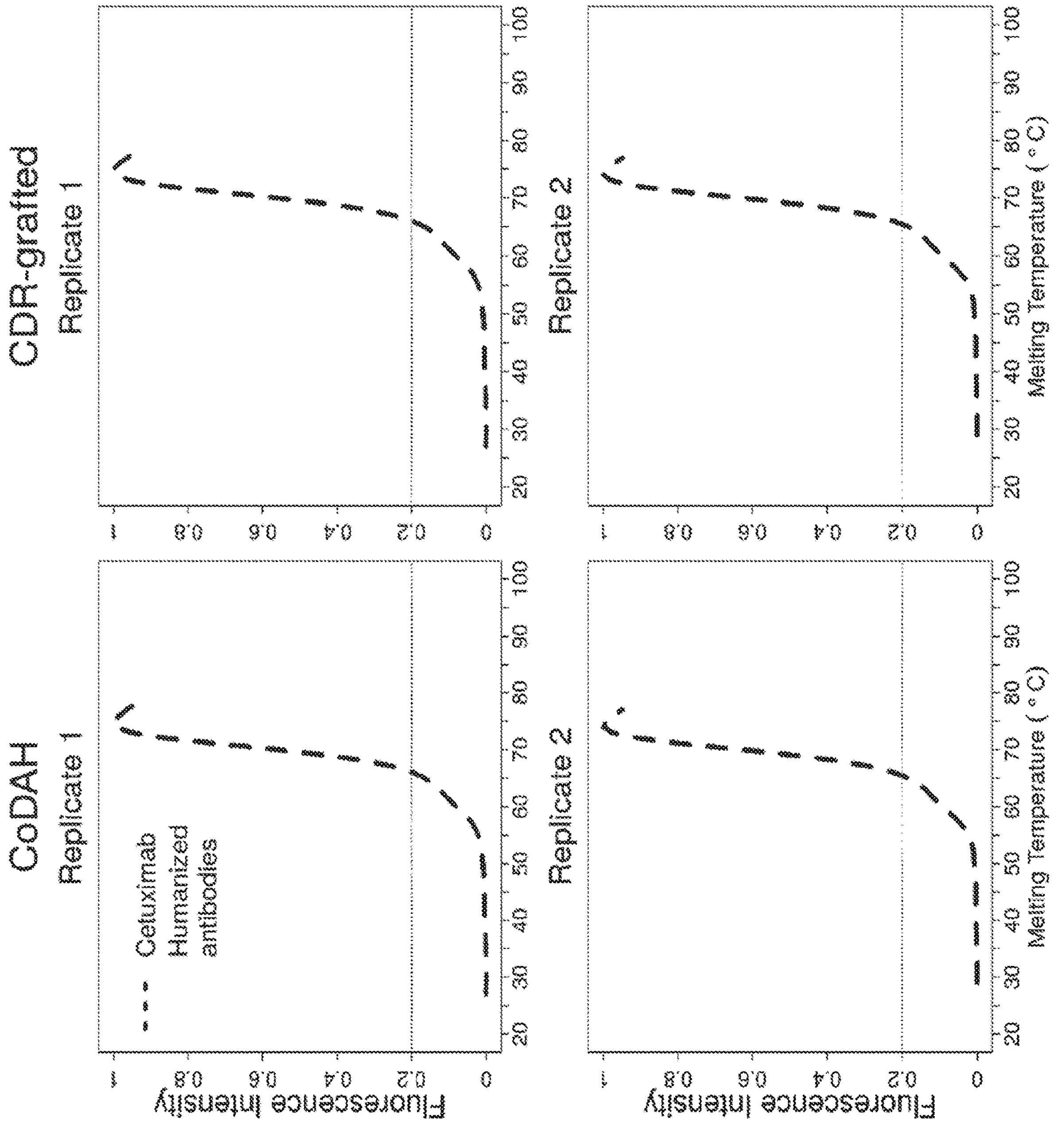
FIG. 5. Differential Scanning Fluorimetry (DSF) melting curves of CoDAH (left) and CDR-grafted (right) designs. The fluorescence intensity values are normalized to corresponding peak values. Shown are replicate traces from two independent measurements (top and bottom, respectively). Grafted designs tended to exhibit multiple transitions, so the TM20* melting point was defined for subsequent comparison based on the first transition above 20% maximum fluorescence intensity (horizontal dashed line). Similar conclusions resulted from other arbitrarily chosen fractional melting cutoffs (see FIG. 7).
Figure 6A:
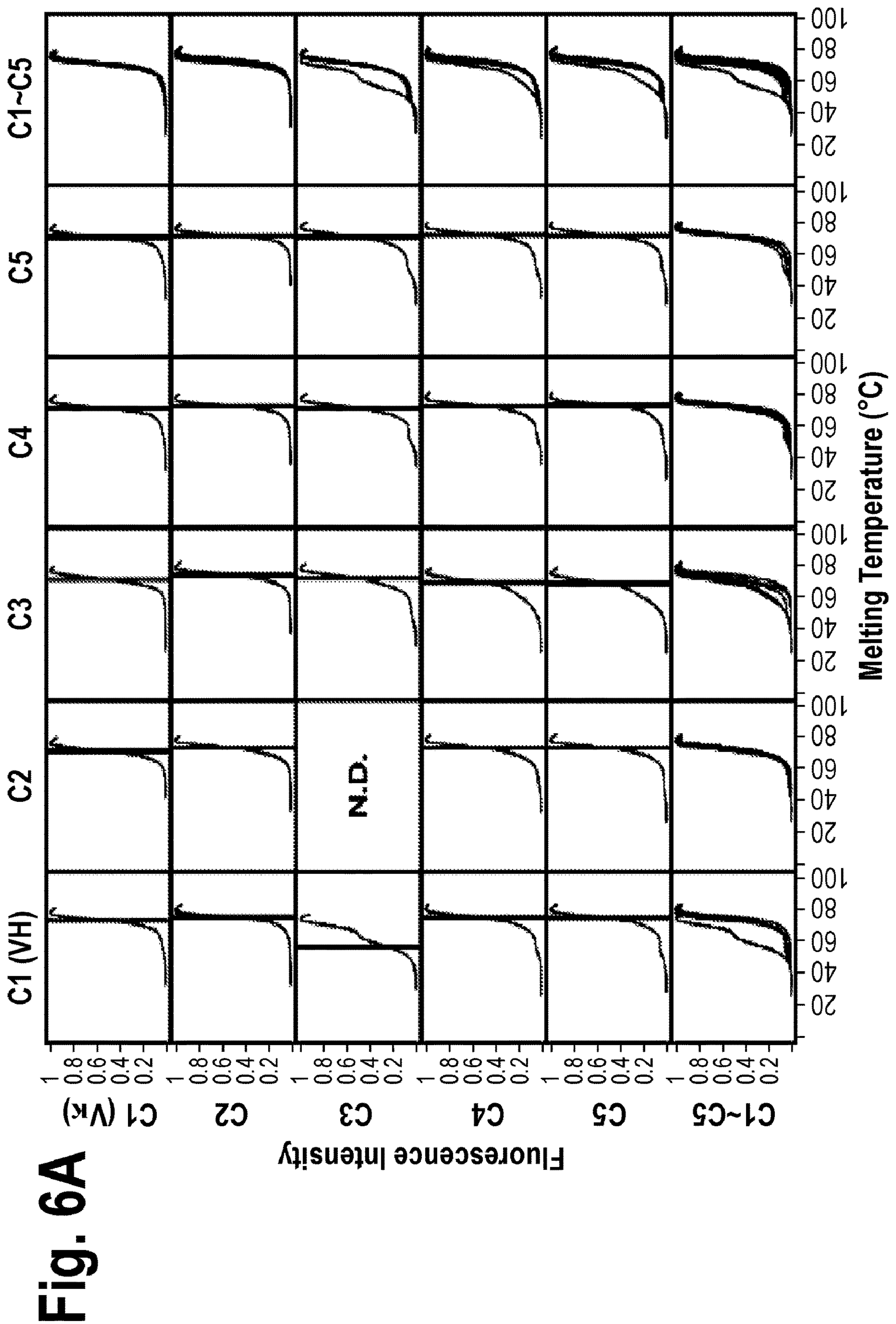
FIG. 6A-D. Melting temperature curves of CoDAH and CDR grafted designs.
Figure 6B:
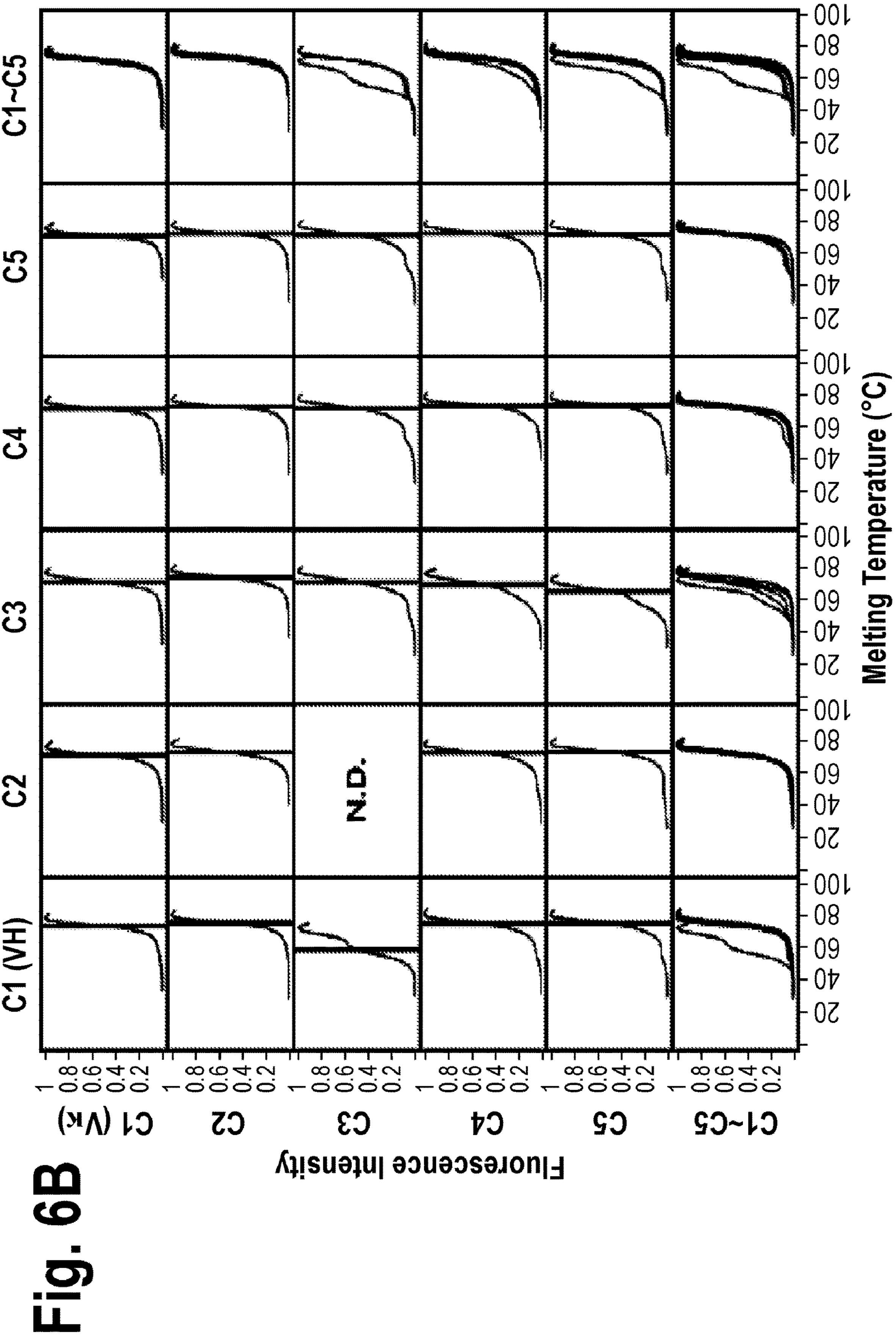
Figure 6C:
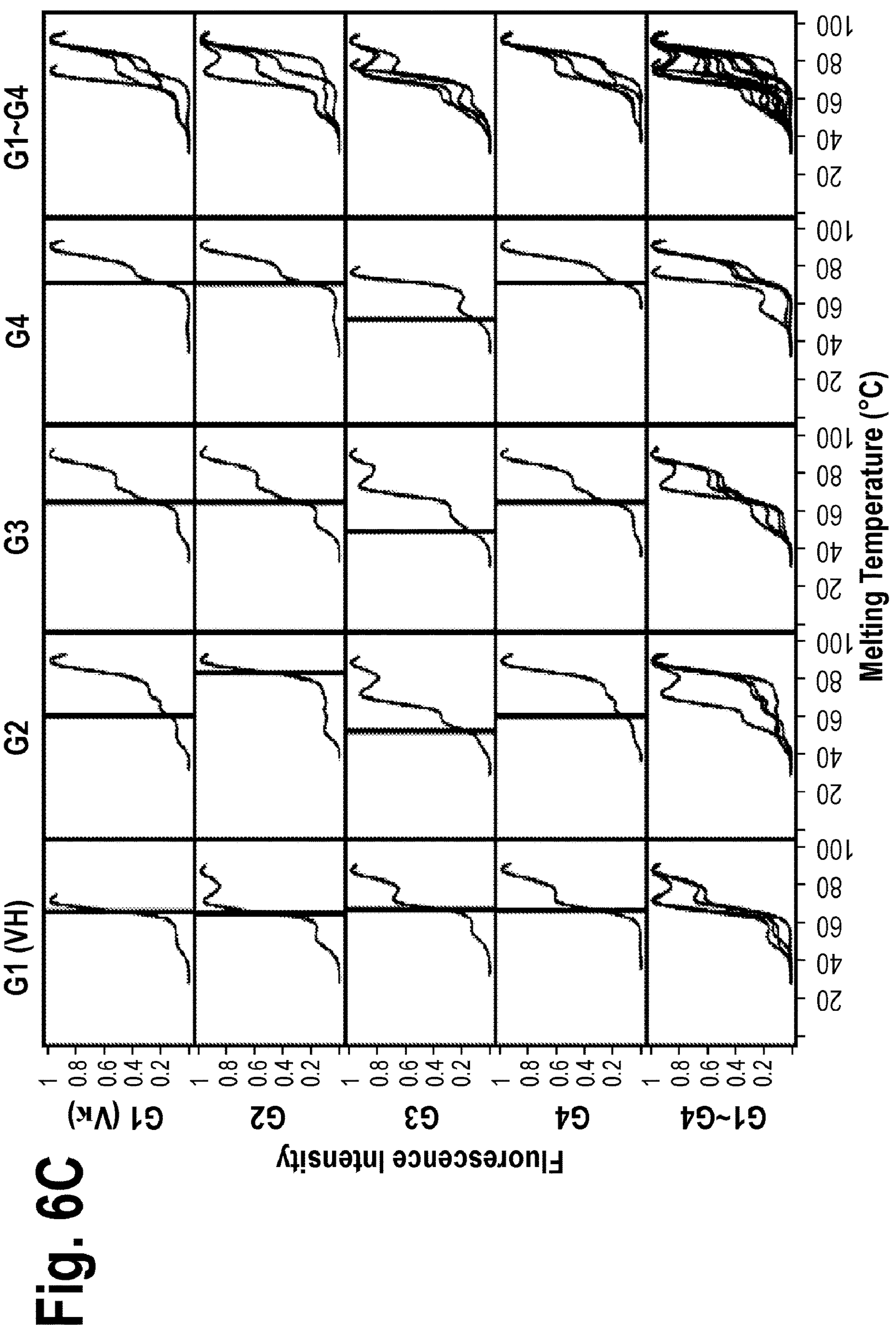
Figure 6D:
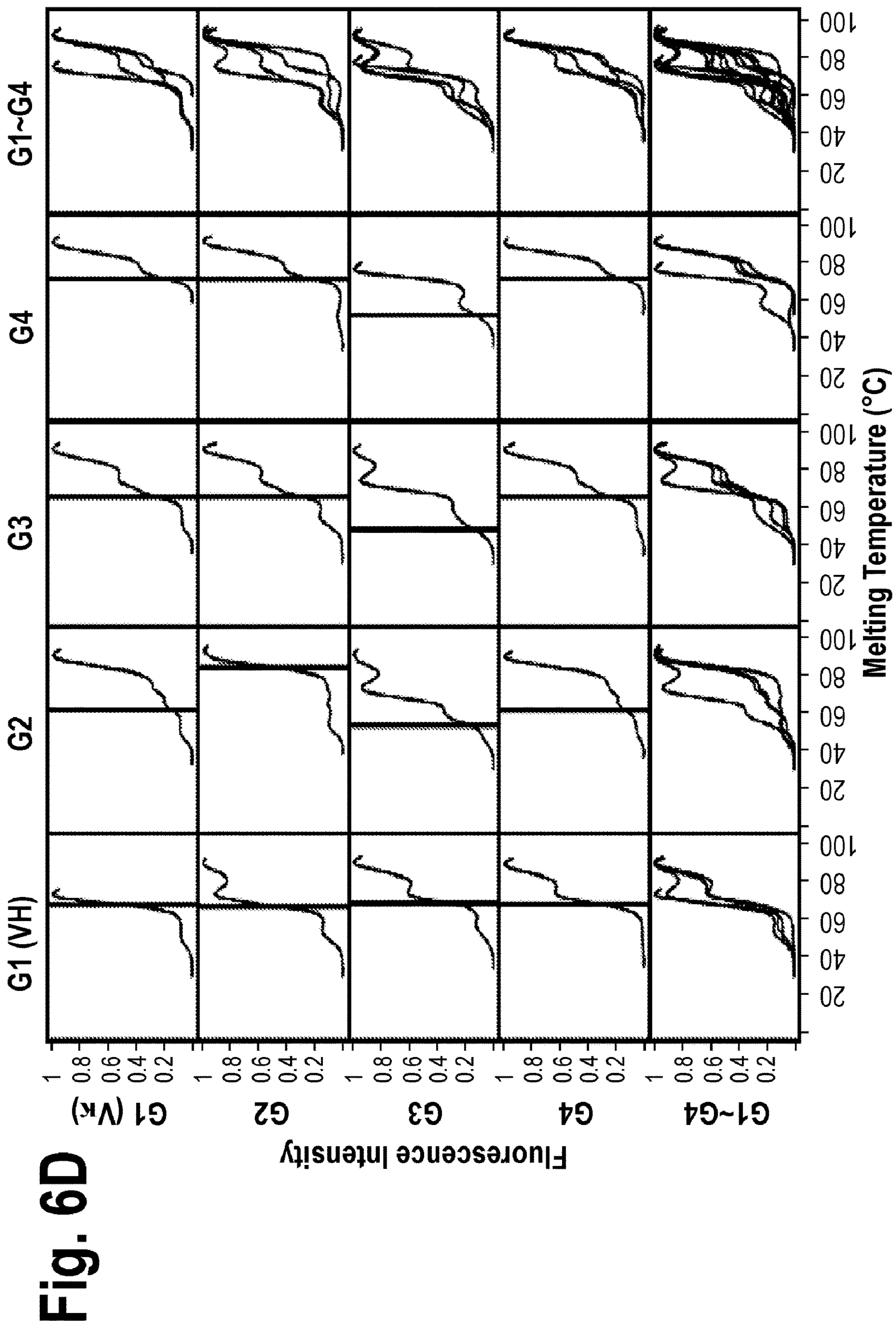
Figure 7:
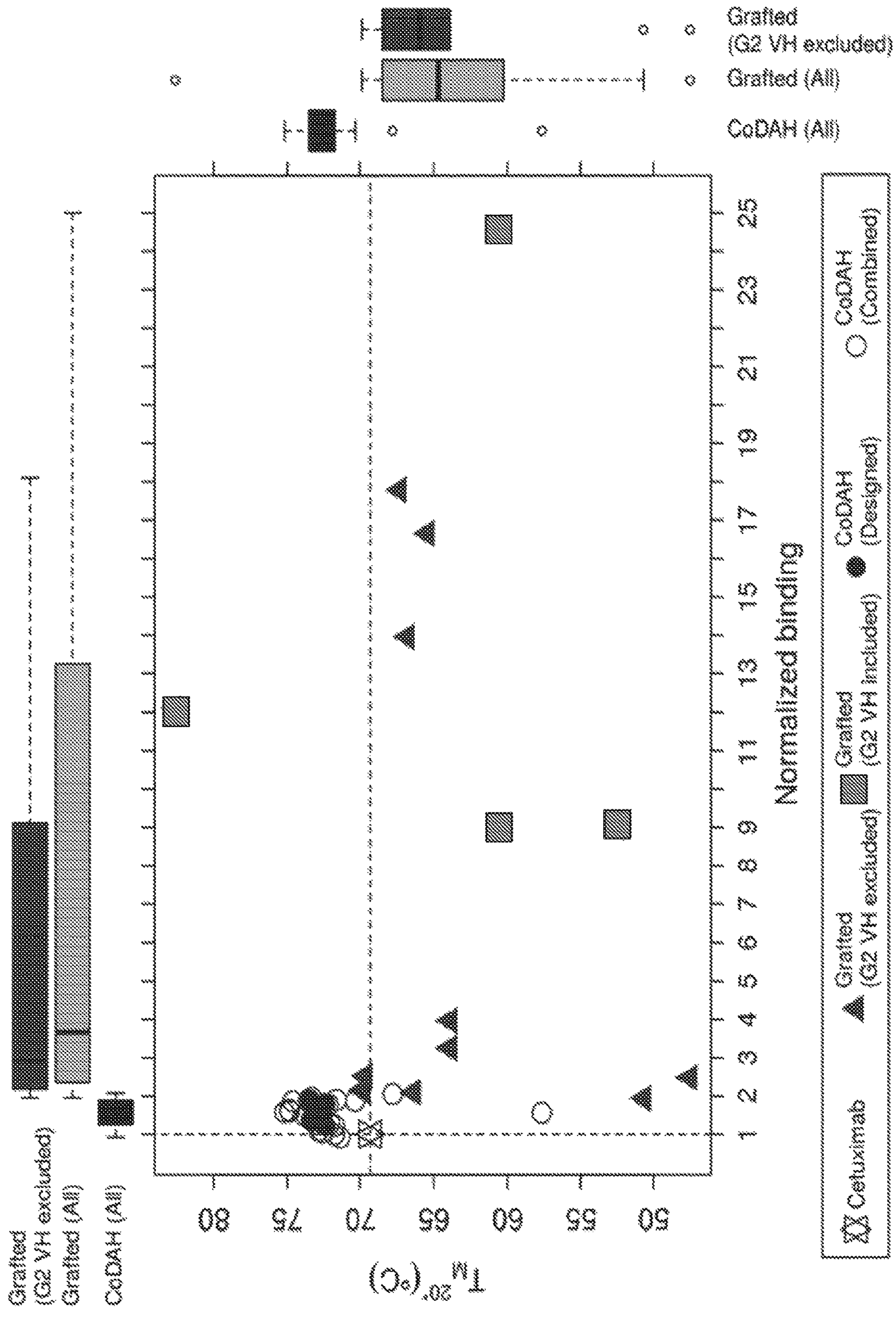
FIG. 7. Binding affinity and TM20* of CoDAH and CDR-grafted designs. Stability of CoDAH designs (circles) was consistently better than that of the parental cetuximab, while binding affinities were near identical to the parental. CDR-grafted variants (triangles and squares) exhibited a wider range of binding affinities and stabilities. In general, grafted designs bearing G2 VH (grey squares), which contains mutations nearby CDR-H2 (FIG. 9), exhibited lower stability and lower binding affinity than the parental cetuximab (star). Box plots for average KD (top), and TM20* (right) values are shown (CoDAH Pareto optimal designs dark solid circle; CoDAH combined designs open circle; grafted including G2 VH square; grafted excluding G2 VH triangle).

Despite the absence of the Fc region, the majority of the CDR-grafted constructs and one of the CoDAH constructs exhibited complex melting curves consisting of two or more transitions (superposition in FIG. 5; individuals in FIG. 6A-D). To facilitate comparison of thermostabilities, a denaturation threshold was chosen to ignore transitions below 20% maximum fluorescence intensity (TM20*); Table S1 considers other thresholds. Using the TM20* cutoff, the five Pareto optimal CoDAH designs exhibited melting temperatures 3.2 to 6.3° C. higher than the parental cetuximab template, and all but two of the cross-paired CoDAH constructs likewise manifested enhanced thermostability (FIG. 7, FIG. 10). The G2 VH/G2 Vκ CDR-grafted design exhibited the single highest TM20* of any antibody in this study, but all other CDR-grafted designs exhibited TM20* values equal to or less than that of cetuximab (FIG. 7, FIG. 10). Additionally, CoDAH designs overwhelmingly exhibited single transition melting curves (FIG. 5, FIG. 6A-B) whereas all CDR-grafted designs manifested multiple transitions (FIG. 5, FIG. 6C-D). Thermostabilities of CoDAH designs were statistically significantly better than those of the grafted ones (p-value <10-6 based on the Kolmogorov-Smirnov test).

The EGFR binding affinities of all antibodies were estimated using biolayer interferometry on a ForteBio Octet Red instrument (ForteBio, Menlo Park, Calif., USA). Purified IgG samples at 12.5 μg/ml in phosphate buffered saline (PBS, 137 mM NaCl, 2.6 mM KCl, 10 mM Na2HPO4, 1.7 mM KH2PO4, pH 7.4) were immobilized on protein A tips (ForteBio) and exposed to 100 nM recombinant, soluble his tagged human EGFR (Sino Biologicals, North Wales, Pa., USA) in PBS. Association and dissociation rates and equilibrium affinity were determined using software provided with the instrument. Samples were analyzed as technical duplicates in two to three independent experiments, estimated KD values were normalized to that of the cetuximab parental antibody, and normalized values were employed for relative ranking of antibody binding activity.

Figure 8:
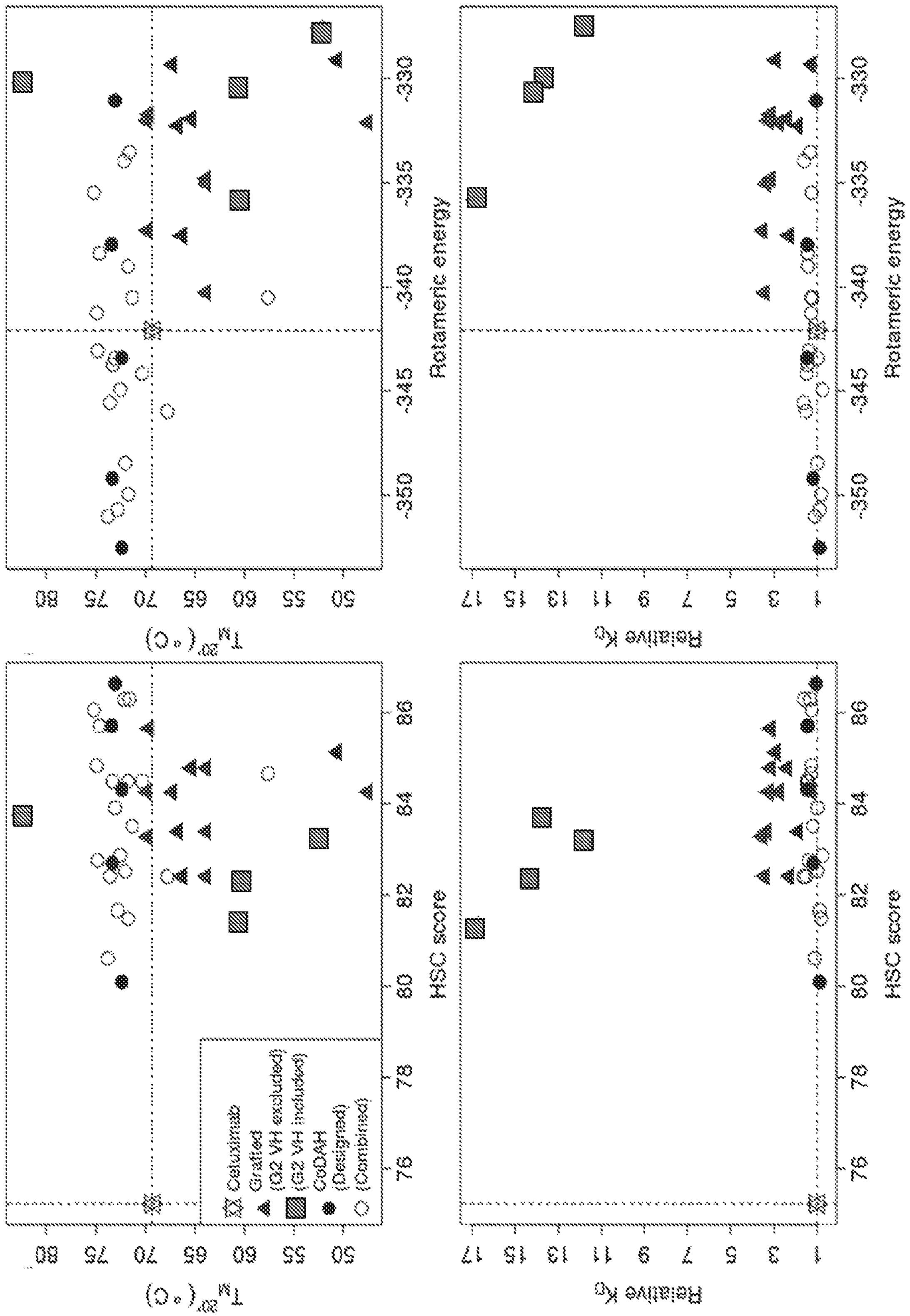
FIG. 8. Experimentally measured stability and binding affinity vs. computational design metrics.

While thermostability analysis was performed on Fab fragments, affinities were measured with full length IgG antibodies. All 25 CoDAH designs (both Pareto optimal and cross-pairs) retained the parental cetuximab binding activity (0.7-1.5-fold, FIG. 7 and Table 1). In contrast, the CDR-grafted designs exhibited a wide range of estimated binding affinities ranging from 1.2 to 16-fold weaker (FIG. 7). The CoDAH designs displayed statistically significantly better KD values than the grafted ones (p-value <10-6 by Kolmogorov-Smirnov). Overall, the 25 CoDAH designs, which spanned a breadth of HSC scores (FIG. 2), exhibited consistent experimental performance (FIG. 7). There was no evident correlation between HSC versus TM20* or KD or between rotameric energy versus TM20* or KD (FIG. 8).

Maintaining stability and binding affinity are critical parallel objectives of antibody humanization projects, but the dominant methods of humanization continue to be largely empirical, relying upon trial and error optimization that can produce widely variable performance outcomes. For example, a recent study using experimentally driven in vitro somatic hypermutation methods yielded a CDR-grafted cetuximab variant with 7° C. improved thermostability but 8-fold loss in binding affinity (McConnell et al., 2013, McConnell et al., 2014). Here, we have demonstrated that computationally humanized cetuximab variants consistently display a combination of increased humanness, substantially improved thermostability, and near wild type binding affinity. While CoDAH is most efficient when drawing upon a large repertoire of germline sequences, here mutable amino acids at each position were selected from only the three VH (IGHV4-4, 34 and 59) and two Vκ (IGKV6D-21 and 41) sequences used for comparative CDR-grafting experiments. Even when focused on the same set of antibody germline sequences and targeting largely similar positions (FIG. 9), the computational algorithm CoDAH tended to employ more stabilizing mutations to better effect than the direct grafting method. It should be noted that neither strategy mutated residues in the VH/Vκ interface region, by explicit exclusion in grafting, and implicitly by modeling in the computational design process.

Figure 11:
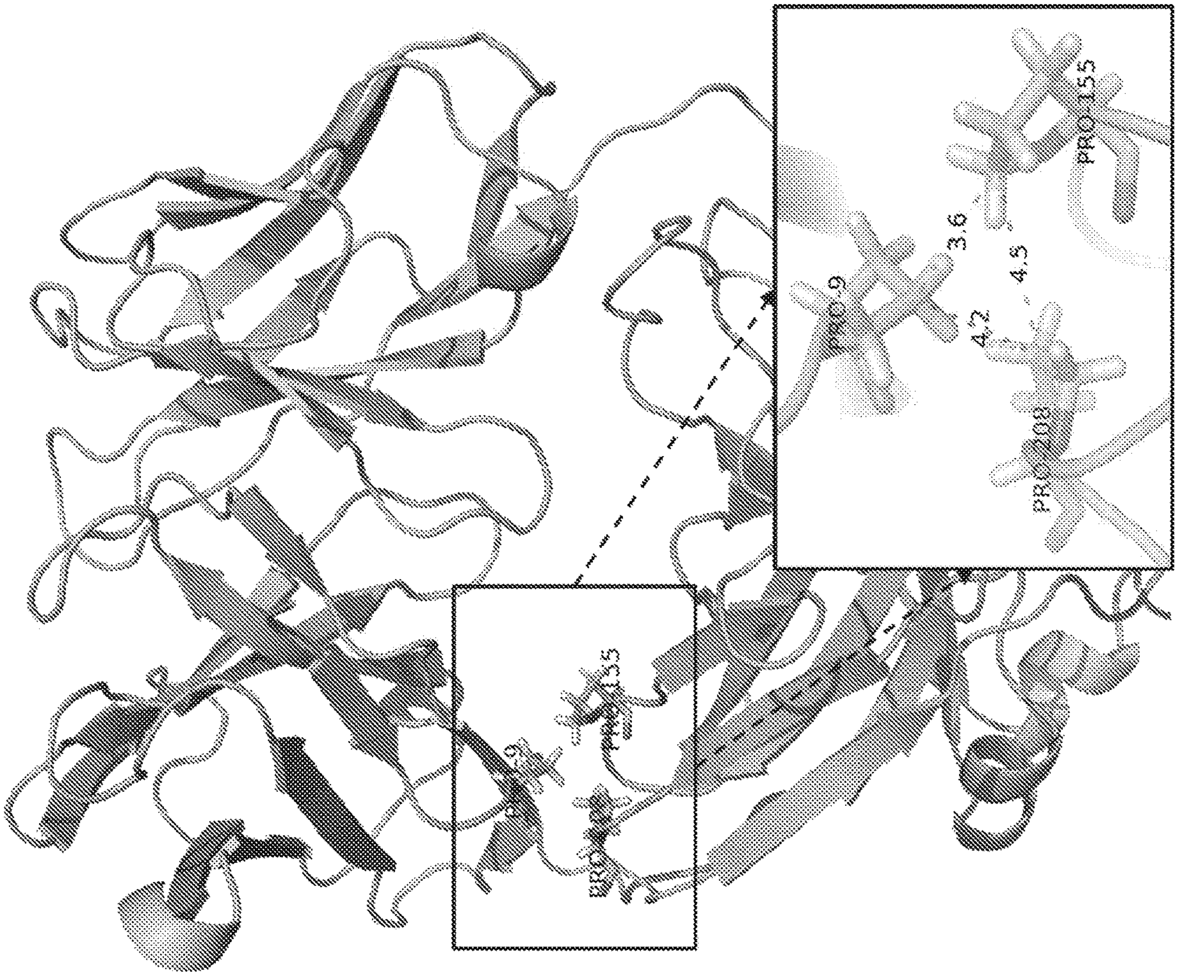
FIG. 11. Inter-domain interaction between VH and CH1. Proline at position 9 of cetuximab (PDB code 1YY8) is in close contact with other proline residues in the CH1 region.

We hypothesize that the multiple transitions observed in the melting curves for grafted designs may come from inter-domain interactions. Interestingly, the P9A mutation of the G2 and G3 VH domains is one of the evident differences among grafted designs (FIG. 9). The proline residue at position 9 in cetuximab seems to be in contact with two proline residues in the CH1 domain (FIG. 11), and mutating the position may cause instability of inter-domain interactions between VH and CH1 (Röthlisberger et al., 2005). Consistent with this hypothesis, grafted constructs bearing the G2 and G3 VH generally exhibited lower thermostability than cetuximab, although the G2 VH/G2 Vκ was an exceptionally stable antibody as measured by TM20*.

It is known that modification of CDRs and their neighboring residues can detrimentally impact binding affinity (Wiens et al., 1998), and CoDAH constructs universally avoided mutations adjacent to CDRs. Likewise, most grafted constructs excluded CDR-adjacent mutations, with the exception of the G2 VH chain, in which substitutions were made at positions 58, 61, 63, and 64. The Kabat and Chothia numbering schemes employ different definitions for CDR positions, and in particular Kabat CDR-H2 is substantially longer (Kabat: residues 50-65, and Chothia: residues 52-56). For G2 VH, the mutated positions were adjacent to CDR-H2 by the Chothia numbering, yet within CDR-H2 by the Kabat (see FIG. 9, underlined italic). These substitutions are likely the dominant driver of poor affinities in designs bearing the G2 VH chain, as those four antibodies were all clear outliers in Octet binding studies (approximately 11 to 16-fold reduction in KD, FIG. 7).

In conclusion, we have demonstrated that the structure-based computational antibody humanization method, CoDAH, is a cost-effective and reliable tool to directly generate humanized antibody variants with high stability and binding affinity. This tool may prove useful for antibody engineers seeking to quickly and effectively humanize antibodies derived from foreign hosts.

REFERENCES

Abhinandan K. and Martin A. C. (2008) Analysis and improvements to Kabat and structurally correct numbering of antibody variable domains. Molecular immunology, 45, 3832-3839

Aggarwal S. R. (2014) What's fueling the biotech engine—2012 to 2013. Nature biotechnology, 32, 32-39

Baca M., Presta L. G., O'Connor S. J. and Wells J. A. (1997) Antibody humanization using monovalent phage display. Journal of Biological Chemistry, 272, 10678-10684

Chen C.-Y., Georgiev I., Anderson A. C. and Donald B. R. (2009) Computational structure-based redesign of enzyme activity. Proceedings of the National Academy of Sciences, 106, 3764-3769

Choi Y., Hua C., Sentman C. L., Ackerman M. E. and Bailey-Kellogg C. (2015) Antibody humanization by structure-based computational protein design. mAbs, 1-13

Chothia C., Gelfand I. and Kister A. (1998) Structural determinants in the sequences of immunoglobulin variable domain. Journal of molecular biology, 278, 457-479

Chothia C., Novotny J., Bruccoleri R. and Karplus M. (1985) Domain association in immunoglobulin molecules: the packing of variable domains. Journal of molecular biology, 186, 651-663

Clark M. (2000) Antibody humanization: a case of the 'Emperor's new clothes'? Immunology today, 21, 397-402

Dall'Acqua W. F., Damschroder M. M., Zhang J., Woods R. M., Widjaja L., Yu J. and Wu H. (2005) Antibody humanization by framework shuffling. Methods, 36, 43-60

Dennis M. S. (2010), Current Trends in Monoclonal Antibody Development and Manufacturing. Springer, pp. 9-28.

Duvall M., Bradley N. and Fiorini R. N. (2011) A novel platform to produce human monoclonal antibodies: The next generation of therapeutic human monoclonal antibodies discovery. MAbs, 3, 203-208

Feldhaus M. J., Siegel R. W., Opresko L. K Coleman J. R., Feldhaus J. M. W., Yeung Y. A., Cochran J. R., Heinzelman P., Colby D. and Swers J. (2003) Flow-cytometric isolation of human antibodies from a nonimmune *Saccharomyces cerevisiae* surface display library. Nature biotechnology, 21, 163-170

Foote J. and Winter G. (1992) Antibody framework residues affecting the conformation of the hypervariable loops. Journal of molecular biology, 224, 487-499

Frokjaer S. and Otzen D. E. (2005) Protein drug stability: a formulation challenge. Nature reviews drug discovery, 4, 298-306

Gainza P., Roberts K. E. and Donald B. R. (2012) Protein design using continuous rotamers. PLoS computational biology, 8, e1002335

Gonzales N. R., Padlan E. A., De Pascalis R., Schuck P., Schlom J. and Kashmiri S. V. (2004) SDR grafting of a murine antibody using multiple human germline templates to minimize its immunogenicity. Molecular immunology, 41, 863-872

Harding F. A., Stickler M. M., Razo J. and DuBridge R. B. (2010) The immunogenicity of humanized and fully human antibodies. Residual immunogenicity resides in the CDR regions mAbs, 2, 256-265

He L., Friedman A. M. and Bailey-Kellogg C. (2012) A divide-and-conquer approach to determine the Pareto frontier for optimization of protein engineering experiments. Proteins: Structure, Function, and Bioinformatics, 80, 790-806

Hermeling S., Crommelin D. J., Schellekens H. and Jiskoot W. (2004) Structure-immunogenicity relationships of therapeutic proteins. Pharmaceutical research, 21, 897-903

Hwang W. Y. K. and Foote J. (2005) Immunogenicity of engineered antibodies. Methods, 36, 3-10

Jarasch A., Koll H., Regula J. T., Bader M., Papadimitriou A. and Kettenberger H. (2015) Developability Assessment During the Selection of Novel Therapeutic Antibodies. Journal of pharmaceutical sciences, 104, 1885-1898

Jawa V., Cousens L. P., Awwad M., Wakshull E., Kropshofer H. and De Groot A. S. (2013) T-cell dependent immunogenicity of protein therapeutics: preclinical assessment and mitigation. Clinical Immunology, 149, 534-555

Jones P. T., Dear P. H., Foote J., Neuberger M. S. and Winter G. (1986) Replacing the complementarity-determining regions in a human antibody with those from a mouse. Nature, 321, 522-525

Khee Hwang W. Y., Almagro J. C., Buss T. N., Tan P. and Foote J. (2005) Use of human germline genes in a CDR homology-based approach to antibody humanization. Methods, 36, 35-42

Kirkpatrick P., Graham J. and Muhsin M. (2004) Cetuximab. Nature reviews drug discovery, 3, 549-550

Lazar G. A., Desjarlais J. R., Jacinto J., Karki S. and Hammond P. W. (2007) A molecular immunology approach to antibody humanization and functional optimization. Molecular immunology, 44, 1986-1998

Lee E.-C., Liang Q., Ali H., Bayliss L., Beasley A., Bloomfield-Gerdes T., Bonoli L., Brown R., Campbell J. and Carpenter A. (2014) Complete humanization of the mouse immunoglobulin loci enables efficient therapeutic antibody discovery. Nature biotechnology, 32, 356-363

Li J., Sai T., Berger M., Chao Q., Davidson D., Deshmukh G., Drozdowski B., Ebel W., Harley S. and Henry M. (2006) Human antibodies for immunotherapy development generated via a human B cell hybridoma technology. Proceedings of the National Academy of Sciences of the United States of America, 103, 3557-3562

Lonberg N. (2008), Therapeutic Antibodies. Springer-Verlag, pp. 69-97.

Lu Z.-J., Deng S.-J., Huang D.-G., He Y., Lei M., Zhou L. and Jin P. (2012) Frontier of therapeutic antibody discovery: the challenges and how to face them. World journal of biological chemistry, 3, 187-196

McCafferty J., Griffiths A. D., Winter G. and Chiswell D. J. (1990) Phage antibodies: filamentous phage displaying antibody variable domains. Nature, 348, 552-554

McConnell A. D., Spasojevich V., Macomber J. L., Krapf I. P., Chen A., Sheffer J. C., Berkebile A., Horlick R. A., Neben S. and King D. J. (2013) An integrated approach to extreme thermostabilization and affinity maturation of an antibody. Protein Engineering Design and Selection, 26, 151-164

McConnell A. D., Zhang X., Macomber J. L., Chau B., Sheffer J. C., Rahmanian S., Hare E., Spasojevic V., Horlick R. A. and King D. J. (2014), mAbs. Taylor & Francis, Nelson A. L., Dhimolea E. and Reichert J. M. (2010) Development trends for human monoclonal antibody therapeutics. Nature reviews drug discovery, 9, 767-774

Niesen F. H., Berglund H. and Vedadi M. (2007) The use of differential scanning fluorimetry to detect ligand interactions that promote protein stability. Nature protocols, 2, 2212-2221

Osbourn J., Groves M. and Vaughan T. (2005) From rodent reagents to human therapeutics using antibody guided selection. Methods, 36, 61-68

Parker A. S., Choi Y., Griswold K. E. and Bailey-Kellogg C. (2013) Structure-guided deimmunization of therapeutic proteins. Journal of Computational Biology, 20, 152-165

Parker A. S., Zheng W., Griswold K. E. and Bailey-Kellogg C. (2010) Optimization algorithms for functional deimmunization of therapeutic proteins. BMC bioinformatics, 11, 180

Pearlman D. A., Case D. A., Caldwell J. W., Ross W. S., Cheatham III T. E., DeBolt S., Ferguson D., Seibel G. and Kollman P. (1995) AMBER, a package of computer programs for applying molecular mechanics, normal mode analysis, molecular dynamics and free energy calculations to simulate the structural and energetic properties of molecules. Computer Physics Communications, 91, 1-41

Pedersen J. T., Henry A. H., Searle S. J., Guild B. C., Roguska M. and Rees A. R. (1994) Comparison of surface accessible residues in human and murine immunoglobulin Fv domains: implication for humanization of murine antibodies. Journal of molecular biology, 235, 959-973

Pendley C., Schantz A. and Wagner C. (2003) Immunogenicity of therapeutic monoclonal antibodies. Current opinion in molecular therapeutics, 5, 172-179

Poiron C., Wu Y., Ginestoux C., Ehrenmann F., Patrice D. and Lefranc M.-P. (2010) IMGT/mAb-DB: the IMGT database for therapeutic monoclonal antibodies. JOBIM, Paper 13

Qiu D., Shenkin P. S., Hollinger F. P. and Still W. C. (1997) The GB/SA continuum model for salvation. A fast analytical method for the calculation of approximate Born radii. The Journal of Physical Chemistry A, 101, 3005-3014

Ratanji K. D., Derrick J. P., Dearman R. J. and Kimber I. (2013) Immunogenicity of therapeutic proteins: Influence of aggregation. Journal of immunotoxicology, 11, 99-109

Retter I., Althaus H. H., Munch R. and Muller W. (2005) VBASE2, an integrative V gene database. Nucleic acids research, 33, D671-D674

Roguska M. A., Pedersen J. T., Keddy C. A., Henry A. H., Searle S. J., Lambert J. M., Goldmacher V. S., Blatter, W A, Rees A. R. and Guild B. C. (1994) Humanization of murine monoclonal antibodies through variable domain resurfacing. Proceedings of the National Academy of Sciences, 91, 969-973

Rosenberg A. S. (2006) Effects of protein aggregates: an immunologic perspective. The AAPS journal, 8, E501-E507

Roskos L. K., Davis C. G. and Schwab G. M. (2004) The clinical pharmacology of therapeutic monoclonal antibodies. Drug development research, 61, 108-120

Röthlisberger D., Honegger A. and Pluckthun A. (2005) Domain interactions in the Fab fragment: a comparative evaluation of the single-chain Fv and Fab format engineered with variable domains of different stability. Journal of molecular biology, 347, 773-789

Schellekens H. (2002) Immunogenicity of therapeutic proteins: clinical implications and future prospects. Clinical therapeutics, 24, 1720-1740

Studnicka G. M., Soares S., Better M., Williams R. E., Nadell R. and Horwitz A. H. (1994) Human-engineered monoclonal antibodies retain full specific binding activity by preserving non-CDR complementarity-modulating residues. Protein engineering, 7, 805-814

Swann P. G., Tolnay M., Muthukkumar S., Shapiro M. A., Rellahan B. L. and Clouse K. A. (2008) Considerations for the development of therapeutic monoclonal antibodies. Current opinion in immunology, 20, 493-499

Wiens G. D., Robert V. A., Whitcomb E. A O'Hare T., Stenzel-Poore M. P. and Rittenberg M. B. (1998) Harmful somatic mutations: lessons from the dark side. Immunological reviews, 162, 197-209.

Additional embodiments are within the claims.

What is claimed is:

1. An isolated anti-EGFR monoclonal antibody or antigen binding portion thereof, the antibody or antigen binding portion thereof comprising a heavy chain and a light chain, and wherein the heavy chain comprises an amino acid sequence selected from the group consisting of SEQ ID NO: 3, 4, 5, 6 and 7 and the light chain comprises an amino acid sequence selected from the group consisting of SEQ ID NO: 8, 9, 10, 11 and 12.

2. The isolated anti-EGFR monoclonal antibody or the antigen binding portion thereof of claim 1, wherein the heavy chain or the light chain is more similar in sequence to a germ-line EGFR antibody sequences than is SEQ ID NO: 1 or SEQ ID NO:2.

3. The isolated anti-EGFR monoclonal antibody or the antigen binding portion thereof of claim 2, wherein the isolated monoclonal antibody or the antigen binding portion thereof is more similar in sequence to a germ-line EGFR antibody sequence than is a counterpart polypeptide comprising SEQ ID NO:1 or SEQ ID NO:2, and wherein the germ line EGFR antibody sequence is selected from the group consisting of SEQ ID NOs.:19-23.

4. A pharmaceutical composition comprising the isolated anti-EGFR monoclonal antibody, or the antigen-binding portion thereof, of claim 1.

5. The isolated anti-EGFR monoclonal antibody or the antigen binding portion thereof of claim 1, wherein the monoclonal antibody or the antigen binding portion thereof is more thermostable than a corresponding isolated monoclonal antibody or an antigen binding portion thereof comprising SEQ ID NO:1 and SEQ ID NO:2 by a melting temperature (TM) of greater than or equal to 0.1° C.

6. The isolated anti-EGFR monoclonal antibody or the antigen binding portion thereof of claim 5, wherein the monoclonal antibody or the antigen binding portion thereof is more thermostable than a corresponding isolated monoclonal antibody or an antigen binding portion thereof comprising SEQ ID NO:1 and SEQ ID NO:2 by a melting temperature (TM) of greater than or equal to 10.0° C.

* * * * *

SEQUENCE LISTING

```
<160> NUMBER OF SEQ ID NOS: 35

<210> SEQ ID NO 1
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Lys Gln Ser Gly Pro Gly Leu Val Gln Pro Ser Gln
1               5                   10                  15
```

-continued

```
Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115


<210> SEQ ID NO 2
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val
            100                 105                 110


<210> SEQ ID NO 3
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Thr Ile Ser Lys Asp Thr Ser Lys Asn Gln Val Ser Leu
65                  70                  75                  80
```

```
Lys Leu Ser Ser Val Thr Ser Asn Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115


<210> SEQ ID NO 4
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Thr Ile Ser Val Asp Thr Ser Lys Asn Gln Val Ser Leu
65                  70                  75                  80

Lys Leu Ser Ser Val Thr Ser Asn Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115


<210> SEQ ID NO 5
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Gln Gln Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Thr Ile Ser Val Asp Thr Ser Lys Asn Gln Val Ser Leu
65                  70                  75                  80

Lys Leu Ser Ser Val Thr Ser Asn Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115
```

-continued

<210> SEQ ID NO 6
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Thr Ile Ser Lys Asp Asn Ser Lys Ser Gln Val Phe Phe
65                  70                  75                  80

Lys Met Asn Ser Leu Gln Ser Asn Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115
```

<210> SEQ ID NO 7
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Gln Val Gln Leu Gln Gln Ser Gly Pro Gly Leu Val Lys Pro Ser Glu
1               5                   10                  15

Thr Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Thr Ile Asn Lys Asp Asn Ser Lys Ser Gln Val Phe Phe
65                  70                  75                  80

Lys Met Asn Ser Leu Gln Ser Asn Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115
```

<210> SEQ ID NO 8
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 8

Asp Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val
            100                 105                 110

<210> SEQ ID NO 9
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Val Leu Thr Gln Ser Pro Val Phe Leu Ser Val Thr Pro Gly
1               5                   10                  15

Glu Lys Val Thr Ile Thr Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val
            100                 105                 110

<210> SEQ ID NO 10
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Leu Leu Thr Gln Ser Pro Val Ile Leu Ser Val Ser Pro Gly
1               5                   10                  15

Glu Arg Val Thr Phe Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Val Glu Ser

```
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val
            100                 105                 110


<210> SEQ ID NO 11
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Val Leu Thr Gln Ser Pro Val Ile Leu Ser Val Ser Pro Gly
1               5                   10                  15

Glu Arg Val Thr Phe Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Gln Gly Thr Lys Leu Glu Leu Lys Arg Thr Val
            100                 105                 110


<210> SEQ ID NO 12
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Ile Val Leu Thr Gln Ser Pro Val Ile Leu Ser Val Ser Pro Gly
1               5                   10                  15

Glu Arg Val Thr Phe Ser Cys Arg Ala Ser Gln Ser Ile Gly Thr Asn
            20                  25                  30

Ile His Trp Tyr Gln Gln Lys Thr Asp Gln Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Gln Gly Thr Lys Leu Glu Leu Lys Arg Thr Val
            100                 105                 110


<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
```

peptide

<400> SEQUENCE: 13

Asn Tyr Gly Val His
1 5

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 14

Val Ile Trp Ser Gly Gly Asn Thr Asp Tyr Asn Thr Pro Phe Thr Ser
1 5 10 15

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 15

Ala Leu Thr Tyr Tyr Asp Tyr Glu Phe Ala Tyr
1 5 10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 16

Arg Ala Ser Gln Ser Ile Gly Thr Asn Ile His
1 5 10

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 17

Tyr Ala Ser Glu Ser Ile Ser
1 5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 18

Gln Gln Asn Asn Asn Trp Pro Thr Thr
1 5

<210> SEQ ID NO 19

-continued

<211> LENGTH: 98
<212> TYPE: PRT
<213> ORGANISM: Homo sapiens

<400> SEQUENCE: 19

Gln Val Gln Leu Gln Glu Ser Gly Pro Gly Leu Val Lys Pro Pro Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Cys Cys
                85                  90                  95

Ala Arg

<210> SEQ ID NO 20
<211> LENGTH: 97
<212> TYPE: PRT
<213> ORGANISM: Homo sapiens

<400> SEQUENCE: 20

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 21
<211> LENGTH: 97
<212> TYPE: PRT
<213> ORGANISM: Homo sapiens

<400> SEQUENCE: 21

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 22
<211> LENGTH: 95
<212> TYPE: PRT
<213> ORGANISM: Homo sapiens

<400> SEQUENCE: 22

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro
                85                  90                  95
```

<210> SEQ ID NO 23
<211> LENGTH: 95
<212> TYPE: PRT
<213> ORGANISM: Homo sapiens

<400> SEQUENCE: 23

```
Asp Val Val Met Thr Gln Ser Pro Ala Phe Leu Ser Val Thr Pro Gly
1               5                   10                  15

Glu Lys Val Thr Ile Thr Cys Gln Ala Ser Glu Gly Ile Gly Asn Tyr
            20                  25                  30

Leu Tyr Trp Tyr Gln Gln Lys Pro Asp Gln Ala Pro Lys Leu Leu Ile
        35                  40                  45

Lys Tyr Ala Ser Gln Ser Ile Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Gly Asn Lys His Pro
                85                  90                  95
```

<210> SEQ ID NO 24
<211> LENGTH: 36
<212> TYPE: PRT
<213> ORGANISM: Artificial Sequence
<220> FEATURE:
<223> OTHER INFORMATION: Polypeptide

<400> SEQUENCE: 24

```
Gly Asp Tyr Ile Tyr Tyr Ala Asp Thr Val Lys Gly Arg Phe Thr Ile
1               5                   10                  15

Ser Arg Asp Asn Ala Arg Asn Thr Leu Tyr Leu Gln Met Ser Ser Leu
            20                  25                  30

Lys Ser Glu Asp
        35
```

<210> SEQ ID NO 25
<211> LENGTH: 36
<212> TYPE: PRT
<213> ORGANISM: Artificial Sequence
<220> FEATURE:
<223> OTHER INFORMATION: Polypeptide

<400> SEQUENCE: 25

Ser Gly Gly Thr Asn Thr Ala Gln Lys Phe Gln Gly Arg Val Thr Ser
1               5                   10                  15

Thr Arg Asp Thr Ser Ile Ser Thr Ala Tyr Met Glu Leu Ser Arg Leu
            20                  25                  30

Arg Ser Asp Asp
        35

<210> SEQ ID NO 26
<211> LENGTH: 35
<212> TYPE: PRT
<213> ORGANISM: Artificial Sequence
<220> FEATURE:
<223> OTHER INFORMATION: Polypeptide

<400> SEQUENCE: 26

Asp Asp Lys Arg Tyr Ser Pro Ser Leu Lys Ser Arg Leu Thr Ile Thr
1               5                   10                  15

Lys Asp Thr Ser Lys Asn Gln Val Val Leu Thr Met Thr Asn Met Asp
            20                  25                  30

Pro Val Asp
        35

<210> SEQ ID NO 27
<211> LENGTH: 36
<212> TYPE: PRT
<213> ORGANISM: Artificial Sequence
<220> FEATURE:
<223> OTHER INFORMATION: Polypeptide

<400> SEQUENCE: 27

Gly Ser Glu Lys Tyr Tyr Val Asp Cys Val Lys Gly Arg Phe Thr Ile
1               5                   10                  15

Ser Arg Asp Asn Ala Lys Asn Ser Leu Tyr Leu Gln Met Asn Ser Leu
            20                  25                  30

Arg Ala Glu Asp
        35

<210> SEQ ID NO 28
<211> LENGTH: 9
<212> TYPE: PRT
<213> ORGANISM: Artificial Sequence
<220> FEATURE:
<223> OTHER INFORMATION: Polypeptide

<400> SEQUENCE: 28

Val Asp Ser Val Lys Gly Arg Phe Thr
1               5

<210> SEQ ID NO 29
<211> LENGTH: 9
<212> TYPE: PRT
<213> ORGANISM: Artificial Sequence
<220> FEATURE:
<223> OTHER INFORMATION: Polypeptide

<400> SEQUENCE: 29

Asp Ser Val Lys Gly Arg Phe Thr Ile
1               5

-continued

<210> SEQ ID NO 30
<211> LENGTH: 9
<212> TYPE: PRT
<213> ORGANISM: Artificial Sequence
<220> FEATURE:
<223> OTHER INFORMATION: Polypeptide

<400> SEQUENCE: 30

```
Ser Val Lys Gly Arg Phe Thr Ile Ser
1               5
```

<210> SEQ ID NO 31
<211> LENGTH: 9
<212> TYPE: PRT
<213> ORGANISM: Artificial Sequence
<220> FEATURE:
<223> OTHER INFORMATION: Polypeptide

<400> SEQUENCE: 31

```
Val Lys Gly Arg Phe Thr Ile Ser Arg
1               5
```

<210> SEQ ID NO 32
<211> LENGTH: 89
<212> TYPE: PRT
<213> ORGANISM: Artificial Sequence
<220> FEATURE:
<223> OTHER INFORMATION: Polypeptide

<400> SEQUENCE: 32

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp
                85
```

<210> SEQ ID NO 33
<211> LENGTH: 87
<212> TYPE: PRT
<213> ORGANISM: Artificial Sequence
<220> FEATURE:
<223> OTHER INFORMATION: Polypeptide

<400> SEQUENCE: 33

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr
```

-continued

```
                85


<210> SEQ ID NO 34
<211> LENGTH: 27
<212> TYPE: PRT
<213> ORGANISM: Artificial Sequence
<220> FEATURE:
<223> OTHER INFORMATION: Polypeptide

<400> SEQUENCE: 34

Lys Gln Pro Val Gln Gln Ser Ile Ser Asp Thr Phe Thr Ser Asn Lys
1               5                   10                  15

Asn Ser Phe Phe Met Asn Leu Gln Ser Asn Ile
            20                  25


<210> SEQ ID NO 35
<211> LENGTH: 21
<212> TYPE: PRT
<213> ORGANISM: Artificial Sequence
<220> FEATURE:
<223> OTHER INFORMATION: Polypeptide

<400> SEQUENCE: 35

Asp Leu Val Ile Leu Ser Gly Arg Ser Phe Ser His Arg Thr Asn Gly
1               5                   10                  15

Ser Arg Ile Ser Ile
            20
```